(12) United States Patent
Simon et al.

(10) Patent No.: US 12,178,906 B2
(45) Date of Patent: Dec. 31, 2024

(54) METHOD OF ADMINISTERING A SELF-FOAMING COMPOSITION

(71) Applicant: JELLYNOV, Chatillon (FR)

(72) Inventors: Jean-Michel Simon, Chatillon (FR); Stéphane Roger, Serres Castet (FR)

(73) Assignee: JELLYNOV, Chatillon (FR)

( * ) Notice: Subject to any disclaimer, the term of this patent is extended or adjusted under 35 U.S.C. 154(b) by 136 days.

(21) Appl. No.: 17/897,690

(22) Filed: Aug. 29, 2022

(65) Prior Publication Data

US 2022/0409529 A1    Dec. 29, 2022

Related U.S. Application Data

(63) Continuation of application No. 16/625,257, filed as application No. PCT/FR2018/051462 on Jun. 19, 2018, now Pat. No. 11,471,407.

(30) Foreign Application Priority Data

Jun. 22, 2017 (FR) ...................................... 1755695

(51) Int. Cl.
| | | |
|---|---|---|
| *A61P 3/04* | (2006.01) | |
| *A23K 20/163* | (2016.01) | |
| *A23L 33/125* | (2016.01) | |
| *A61K 9/00* | (2006.01) | |
| *A61K 9/48* | (2006.01) | |
| *A61K 31/734* | (2006.01) | |
| *C08J 9/08* | (2006.01) | |

(52) U.S. Cl.
CPC .......... *A61K 9/0065* (2013.01); *A23K 20/163* (2016.05); *A23L 33/125* (2016.08); *A61K 9/0056* (2013.01); *A61K 9/4866* (2013.01); *A61K 31/734* (2013.01); *A61P 3/04* (2018.01); *C08J 9/08* (2013.01); *A23V 2002/00* (2013.01); *C08J 2203/02* (2013.01); *C08J 2205/022* (2013.01); *C08J 2205/026* (2013.01); *C08J 2205/028* (2013.01); *C08J 2207/10* (2013.01); *C08J 2305/04* (2013.01)

(58) Field of Classification Search
CPC ........ A61K 9/1652; A61K 9/0065; A61P 3/04
See application file for complete search history.

(56) References Cited

U.S. PATENT DOCUMENTS

| | | | |
|---|---|---|---|
| 5,750,585 A | * | 5/1998 | Park .................... A61K 9/122 521/143 |
| 5,840,777 A | | 11/1998 | Eagles et al. |
| 6,018,033 A | | 1/2000 | Chen et al. |
| 6,271,278 B1 | | 8/2001 | Park et al. |
| 6,677,318 B1 | | 1/2004 | Beisel |
| 7,854,745 B2 | | 12/2010 | Brister et al. |
| 8,287,562 B2 | | 10/2012 | Kasic |
| 2003/0021832 A1 | | 1/2003 | Scherr |
| 2005/0137272 A1 | | 6/2005 | Gaserod et al. |
| 2007/0248642 A1 | | 10/2007 | Dornish et al. |
| 2008/0089940 A1 | | 4/2008 | Omidian et al. |
| 2009/0093838 A1 | | 4/2009 | Paganon |
| 2010/0100115 A1 | | 4/2010 | Soetermans et al. |
| 2010/0234233 A1 | | 9/2010 | Sannino et al. |
| 2014/0087056 A1 | | 3/2014 | Yan |
| 2014/0106032 A1 | | 4/2014 | Dardelle et al. |

FOREIGN PATENT DOCUMENTS

| | | | |
|---|---|---|---|
| CN | 105 582 029 A | 5/2016 | |
| WO | 94/00512 A1 | 1/1994 | |
| WO | WO-9511667 A1 * | 5/1995 | ........... A61K 9/0065 |
| WO | 2004/056343 A1 | 7/2004 | |
| WO | 2005/044026 A1 | 5/2005 | |
| WO | 2005/101983 A2 | 11/2005 | |
| WO | 2007/103208 A2 | 9/2007 | |
| WO | 2008/157318 A2 | 12/2008 | |

OTHER PUBLICATIONS

Sharma et al., "Fabrication and Characterization of Natural Origin Chitosan-Gelatin-Alginate Composite Scaffold by Foaming Method Without Using Surfactant," Journal of Applied Polymer Science, 2013, pp. 3228-3241.

Bertrand et al., "Dynamics of swelling and drying in a spherical gel," Phys. Rev. Applied, 2016, vol. 6, pp. 1-19.

Aug. 6, 2018 International Search Report issued in International Patent Application No. PCT/FR2018/051462.

Dec. 24, 2019 International Preliminary Report on Patentability issued in International Patent Application No. PCT/FR2018/051462.

Lau et al; "Effect of polymer ratio and calcium concentration on gelation properties of gellan/gelatin mixed gels", Food Research International 34 (2001) 879-886.

* cited by examiner

*Primary Examiner* — Johann R Richter
*Assistant Examiner* — Danielle Johnson
(74) *Attorney, Agent, or Firm* — Oliff PLC

(57) ABSTRACT

A method for managing and/or treating obesity and/or overweight and/or for inducing weight loss. The method includes orally administering to a patient a composition capable of being transformed into a hydrogel foam after its introduction into the patient stomach. The hydrogel foam occupies at least 20% of the volume of the patient stomach.

23 Claims, 2 Drawing Sheets

METHOD OF ADMINISTERING A SELF-FOAMING COMPOSITION

CROSS REFERENCE TO RELATED APPLICATIONS

Figure 1A:
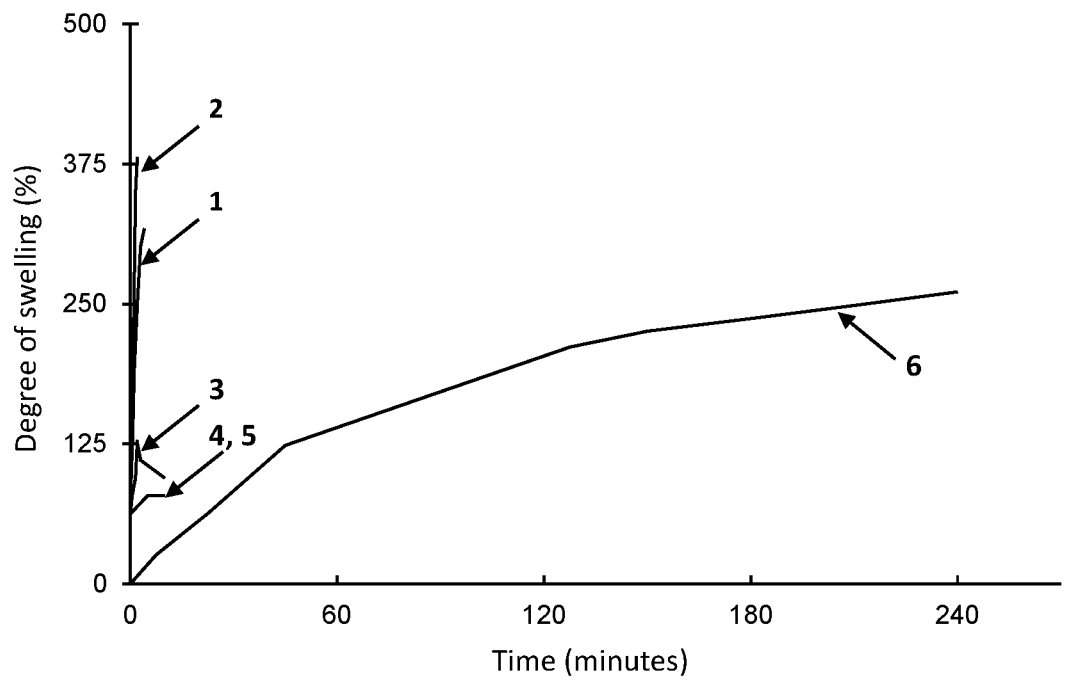

This is a Continuation of application Ser. No. 16/625,257 filed Dec. 20, 2019, which in turn is a national stage entry of PCT/FR2018/051462 filed Jun. 19, 2018, which claims priority to FR 1755695 filed Jun. 22, 2017. The disclosure of the prior applications is hereby incorporated by reference herein in its entirety.

TECHNICAL FIELD

The present invention relates to a polymer composition that is self-foaming in an acid medium, the method for obtaining same as well as the use thereof as a drug, in particular in the treatment of obesity, excess weight or in the context of treatments for preventing diabetes, both human and animal.

PRIOR ART

Excess weight affects 1.4 billion people 20 years of age and over in the world (global estimates of the World Health Organization). By 2030, the number of people overweight is expected to reach 3.3 billion. Excess weight and obesity represent the fifth risk factor for death globally and at least 2.8 million fall victim each year (Source: World Health Organization—"Obesity and excess weight"—Notes, No. 311).

In France, 6.5 million people are considered to be obese (i.e. 14.5% of the adult population). The proportion of obese people rose from 8.5% to 14.5% between 1997 and 2009. The increase in prevalence is observed in all age groups of the population, including seniors, and it seems greater for women (15.1%) than men (13.9%) (Source: Enquête épidémiologique ObÉpi [ObÉpi epidemiological survey]—Roche 2009). It is more particularly the many associated problems such as cardiovascular diseases, diabetes, sleep apnea and problems with joints that represent a risk in people who are overweight or obese.

There are currently six major areas of research and development relating to new treatments against obesity: (1) diets, food supplements and treatments; (2) pharmacological treatments using specific drugs; (3) gastric simulation using implantable electronic devices; (4) invasive surgical procedures involving gastric reduction; (5) intragastric balloons for reducing gastric volume and producing a sensation of satiety; and (6) administration of fiber or of polymeric compounds that swell in the patient's stomach and prevent expulsion thereof via the pylorus, producing a sensation of satiety. These self-swelling substances are then broken down chemically and expelled from the body by the natural routes and by the natural gastrointestinal peristalsis.

Various diets, food supplements, or drugs have now been developed for treating obesity, but none gives significant real benefits. Moreover, certain medical products used in the treatment of obesity have been linked to many serious diseases that are life-threatening for patients. To date, there are no supplements or drugs on the market that have proved effective in reducing the weight of obese people.

Starting out from this finding, the medical sector has developed extreme methods for combating severe obesity or morbid obesity. For example, we may mention surgical methods such as gastroplasty and notably calibrated vertical gastroplasty with gastric resection ("sleeve gastrectomy") or gastric bypass. These surgical methods are relatively effective but they are often irreversible and require extensive postoperative follow-up throughout the patient's life.

Progress has been made with the introduction of gastric balloons as described in patents FR 2897529, US 2010100115 and U.S. Pat. No. 7,854,745. These balloons are introduced into the stomach by surgery or by endoscopy, in the deflated state, and are then inflated (partially) by release or injection of air or else by injection of a saline solution or a normal saline solution, depending on the volume of the patient's stomach. The aim of this type of balloon is to reduce the effective volume of the stomach artificially, with a view to giving the patient a sensation of satiety so as to reduce the intake of calories. However, the expected effect has not really been demonstrated thus far. Moreover, this type of device is usable for a limited time (6 months on average) and must be removed before optionally repeating the operation. These gastric balloons also cause some secondary problems such as ulcers notably owing to the materials used for making the balloons (silicone), which are incompatible with contact with the stomach wall. More seriously, partial or complete deflation of these gastric balloons could cause considerable damage by creating a gastric blockage and obstructing the pylorus. Methods of this type also require follow-up by healthcare professionals throughout the treatment, which is expensive.

There are now more and more so-called natural "appetite suppressants", based on natural fibers that swell in the presence of appreciable quantities of liquid (water) such as konjac, apple pectin, guar gum, agar-agar, or carob gum. These products will fill the patient's stomach like a gastric balloon will. These appetite suppressants moderate the patient's appetite but without producing a sensation of satiety. Moreover, compounds of this type may eventually be responsible for deficiencies in the patient. These compounds are ingested by the patient in the form of a powder and with a relatively large amount of water (from 500 mL to 1 L) in order to allow them to dissolve or disperse, and then swell in connection with hydration of the chains of the polymers of which they are composed. The time for dissolution or dispersion and swelling of the polymer chains is long and may reach almost 1 h, requiring organization of the patient before each meal. There has not been any scientific study demonstrating the real efficacy of these products. Moreover, they are associated with many uncomfortable side-effects (bloating, abdominal pains and even diarrhea).

More recently, the use of super-absorbent hydrogels and hydrogel foams with swelling or even ultra-swelling properties has been developed to facilitate reduction of gastric volume in the context of treatment of obesity.

In particular, US 2010/0234233 A1 describes the preparation of compositions of the hydrogel type starting from at least one hydrophilic polymer, and by crosslinking with a polycarboxylic acid, notably citric acid, as well as use thereof in the treatment of obesity.

U.S. Pat. No. 8,287,562 B2 describes the preparation of devices that can be ingested and are capable of swelling in the gastric environment. These devices are in the form of a self-swelling material, notably a hydrogel that expands in the presence of water, encapsulated in a composite membrane that is soluble in the gastric environment. This type of device is advantageous in that the self-swelling compound does not swell before it reaches the stomach.

WO 2004/056343 A1 describes the use of modified polymers for making hydrogels that are easily degradable in the intestinal environment but not in the gastric environment.

Hydrogel foams have also been developed, with the idea of increasing the capacity of the hydrogels for absorbing water, by means of a porous structure.

These hydrogel foams are obtained by dissolving one or more polymers and by the introduction/bubbling of a gas that will be trapped in the polymer matrix by crosslinking.

U.S. Pat. No. 6,018,033 describes the preparation of saccharide monomers for making hydrogels and hydrogel foams by polymerization/crosslinking. The hydrogel foams are obtained by the introduction of gases during polymerization and by decomposition of a foaming agent such as sodium bicarbonate $NaHCO_3$.

U.S. Pat. No. 5,750,585 describes the preparation of foam of the hydrogel type with super-absorbent properties by introduction of a gas during polymerization of a solution comprising at least one hydrophilic monomer of the olefinic type and a crosslinking agent of the polyolefin type. The gas is produced by decomposition of a foaming agent and notably sodium bicarbonate $NaHCO_3$.

U.S. Pat. No. 6,271,278 B1 describes the preparation of super-porous hydrogel composites by polymerization of a composition comprising at least one ethylenically unsaturated monomer and a crosslinking agent of the polyolefin type in the presence of particles of a disintegrant serving for improving the mechanical properties of the structure and a foaming agent, notably sodium bicarbonate $NaHCO_3$ in order to generate a gas during polymerization.

However, the foam structure of this type of device is obtained before ingestion by the patient, during preparation of said device. The use of these devices therefore involves ingestion of a relatively large volume of hydrogel foam by the patient.

Moreover, all of the hydrogels and hydrogel foams described above are obtained by chemical crosslinking of the polymers. This irreversible crosslinking of the polymers presents the drawback that it makes the aforesaid devices difficult to digest.

U.S. Pat. No. 6,677,318 B1 describes foams of the hydrogel type obtained by ionic and covalent crosslinking of polysaccharide polymers comprising uronic acid units and ingestion thereof in order to provide a sensation of satiety.

However, the foam structure of this device is obtained before ingestion, which means a large volume of device has to be ingested by the patient.

US 2014/0087056 A1 describes food supplements in the form of compositions comprising at least one cationic polymer and an anionic polymer gellable in an acid medium, notably in a gastric environment.

These food supplements may notably comprise basic compounds such as sodium or potassium (bi)carbonate used in order to delay gelation of the system. In fact, the amount of salts used is not sufficient to lead to formation of a foam.

All of the devices of the hydrogel type and hydrogel foams described above make it possible to give the patient a sensation of satiety by swelling of the device in the stomach connected with absorption of water.

Thus, these devices have the drawback of requiring prior ingestion by the patient of a large amount of water (from 500 mL to 1 L) so as to allow them to swell.

Moreover, these devices are of relatively low efficacy and in particular have a relatively long time of action (several hours) to reach maximum swelling of the product. Thus, many of these products require the product to be taken by the oral route 30 to 60 min before a meal.

As a result, these devices require particular organization on the part of the patient, before each meal, which may be complicated for some patients.

Finally, some of these devices have undesirable effects on the digestion.

US 2005/0137272 discloses the preparation of foams based on gelled biopolymers. These foams are usable in the biomedical field but also in the field of personal care or in nutrition.

The document Chhavi Sharma et al., *Journal of Applied Polymer Science*, 2013, p. 3228-3241, discloses the preparation of a composite material based on chitosan, gelatin and alginate by foaming. The material obtained is usable for making support materials for tissue engineering.

U.S. Pat. No. 584,077 and WO 94/00512 teach the preparation of a foam based on polysaccharides by mechanical foaming of an aqueous solution comprising said soluble polysaccharide.

WO 2005/044026 discloses the preparation of a filler usable in smoking articles. The filler is obtained from a foaming agent, an agent capable of crosslinking by the formation of chemical bonds, and a crosslinking agent.

WO 2008/157318 discloses a composite material comprising a foam whose pores are filled with a polysaccharide gel, said material being coated with a layer based on polysaccharide. This material has many applications notably in the biomedical field, personal care and nutrition.

WO 2007/103208 teaches the preparation of an absorbent foam in dry form, having open porosity. This absorbent foam is obtained by foaming an aqueous dispersion comprising an enzymatically degradable biopolymer and a foaming agent, followed by a drying step.

US 2007/0248642 teaches the preparation of a foam gelled by aeration of a dispersion comprising a polysaccharide, ions capable of causing gelation of the polysaccharide and optionally a plasticizer.

US 2003/0021832 teaches the preparation of foam products starting from silver alginate. The foam products obtained are usable for making medical and/or veterinary dressings.

None of these documents discloses self-foaming compositions that can be ingested and that expand in an acid medium.

Consequently, there is still a need for polymer compositions usable for preventing and/or treating obesity that can be used noninvasively and allow a prolonged and controlled reduction of the gastric volume with the aim of facilitating weight loss. There is also still a need for polymer compositions having high degrees of swelling and capable of expanding in a very short time so as to give the patient a sensation of satiety as quickly as possible. There is also still a need to provide compositions allowing reduction of the gastric volume without requiring any other step apart from its ingestion and notably without requiring prior ingestion of water. Finally, there is still a need for compositions capable of being absorbed and whose absorption can be controlled.

SUMMARY OF THE INVENTION

The present invention is based on formulation of a polymer composition capable of being transformed into a hydrogel foam very rapidly, in which this hydrogel foam has a very high degree of swelling in a few minutes. More particularly, the present invention relates to a composition capable of being transformed into a hydrogel foam following its introduction into, or on being brought into contact with, an acid medium, notably at a pH less than or equal to 5, preferably from 0.5 to 5. The composition of the present invention may be used as a food supplement or as a drug in the context of combating obesity or in the context of prophylactic treatment of diabetes both for humans and for animals. This material is absorbable and its absorption can be controlled, which allows it to pass through the pylorus without risk of intestinal obstruction.

The invention relates firstly to a composition comprising:
- at least one hydrophilic polymer selected from polysaccharides, polysaccharide derivatives and mixtures thereof,
- at least one compound capable of crosslinking the hydrophilic polymer by forming ionic bonds,
- at least one foaming agent, and
- at least one foam stabilizer.

The composition according to the invention preferably comprises:
- at least one hydrophilic polymer selected from polysaccharides, polysaccharide derivatives and mixtures thereof,
- at least one compound capable of crosslinking the hydrophilic polymer by forming ionic bonds, selected from salts of divalent cations, salts of trivalent cations and mixtures thereof,
- at least one foaming agent selected from salts capable of decomposing into gas and into monovalent cations, and
- at least one foam stabilizer.

The hydrophilic polymer present in the composition according to the invention is preferably selected from alginates.

Preferably, the composition according to the invention has a content by weight of hydrophilic polymer from 10% to 99.5%, preferably from 15% to 99%, and even more preferably from 15% to 80% relative to the total weight of the composition, the contents being expressed in weight of dry matter.

Advantageously, the compound capable of crosslinking the hydrophilic polymer by forming ionic bonds is selected from divalent cations, trivalent cations and mixtures thereof, preferably selected from divalent cations, more preferably selected from calcium(II), manganese(II), silver(II), iron(II), copper(II), magnesium(II) and mixtures thereof, and is even more preferably calcium(II).

Preferably, the compound capable of crosslinking the hydrophilic polymer by forming ionic bonds comprises at least one metal salt, preferably at least one metal salt having a pKa less than or equal to 6, preferably less than or equal to 5.

Even more preferably, the compound capable of crosslinking the hydrophilic polymer by forming ionic bonds is present in the composition in the form of calcium carbonate $CaCO_3$.

The foaming agent is preferably selected from the salts of monovalent cations.

Preferably, the foaming agent comprises at least one metal salt, preferably at least one metal salt having a pKa less than or equal to 6, and even more preferably less than or equal to 5.

Even more preferably, the foaming agent is selected from carbonate salts, bicarbonate salts and mixtures thereof, preferably it is sodium bicarbonate $NaHCO_3$.

Advantageously, the ratio of the quantity of divalent and/or trivalent cations to the quantity of monovalent cations is greater than or equal to 0.05, preferably greater than or equal to 0.5, the quantities of cations being expressed in moles.

More advantageously, the ratio of the quantity of divalent cations to the quantity of monovalent cations is greater than or equal to 0.05, preferably greater than or equal to 0.5, the quantities of cations being expressed in moles.

Preferably, the foam stabilizer is selected from structure-forming agents, surfactants and mixtures thereof.

According to a first embodiment, the foam stabilizer is selected from structure-forming agents, preferably from proteins, salts thereof and mixtures thereof, and even more preferably from gelatin, albumin, ovalbumin, milk casein, lecithin, sodium caseinate, and mixtures thereof.

According to a second embodiment, the foam stabilizer is selected from nonionic surfactants.

According to a certain embodiment, the composition according to the invention further comprises at least one water-swelling polymer that cannot be crosslinked by the formation of ionic bonds, preferably selected from starch, agar-agar, carrageenan λ (lambda), noncrosslinkable celluloses and mixtures thereof.

According to a first embodiment, the composition according to the invention is a hydrogel.

According to a second embodiment, the composition according to the invention is in dry form, and is notably a xerogel, an aerogel or a cryogel.

The invention also relates to a method for making a composition according to the invention comprising introducing the following into an aqueous medium:
- the hydrophilic polymer,
- the foaming agent,
- the compound capable of crosslinking the polymer by forming ionic bonds, and
- the foam stabilizer.

According to a preferred embodiment, this method comprises the following steps:
(1) dissolving or dispersing the hydrophilic polymer in water, with stirring,
(2) with stirring, dispersing the foaming agent and the compound capable of crosslinking the hydrophilic polymer by forming ionic bonds until a homogeneous dispersion is obtained,
(3) adding the foam stabilizer,
(4) optionally drying the composition.

The invention also relates to a capsule with a core/shell structure comprising at least one core consisting of a composition according to the invention and at least one coating layer covering all or part of the core.

The invention also relates to a composition according to the invention for use as a drug, preferably for preventing and/or treating obesity.

The invention also relates to a dietary kit comprising at least, in two separate parts of one and the same packaging:
- a composition according to the invention,
- a portion of foodstuffs.

The invention also relates to a feed composition for animals in the form of pellets, snacks or biscuits comprising a composition according to the invention and a portion of feed.

The invention finally relates to a device for oral administration comprising a syringe, the body of which is filled with a composition according to the invention.

The invention is advantageous in that it supplies polymer compositions usable for preventing and/or treating obesity which are usable noninvasively and allow a prolonged and controlled reduction of the gastric volume.

The invention is also advantageous in that it proposes a composition that has a high degree of swelling, thus making it possible to reduce the gastric volume by ingesting a limited amount of the composition.

The invention is also advantageous in that the maximum swelling of the composition is reached rapidly. This fast rate of swelling has the consequence that the patient feels a sensation of satiety shortly after ingesting the composition. This results in a quicker and therefore more effective appetite suppressing effect.

The invention is also advantageous in that the device is easily eliminated by the body owing to crosslinking that is predominantly, preferably essentially ionic.

The invention is also advantageous in that it does not require prior ingestion of a liquid and notably of water.

The invention is also advantageous in that the composition is low-calorie and therefore suitable for the treatment and/or prevention of obesity including in persons with diabetes.

Finally, the invention is advantageous in that the composition is absorbable and in that its absorption is controllable.

DETAILED DESCRIPTION

The expression "consists essentially of" followed by one or more features signifies that, besides the components or steps explicitly enumerated, components or steps that do not significantly alter the properties and characteristics of the invention may be included in the method or the material of the invention.

The expression "between X and Y" includes the limits, unless explicitly stated otherwise. This expression therefore signifies that the intended range includes the values X, Y and all the values from X to Y.

The different embodiments, variants, preferences and advantages described above for each of the objects of the invention apply to all the objects of the invention and may be taken separately or in combination.

"Polymer" means, in the sense of the invention, oligomers, prepolymers, homopolymers but also copolymers.

"Hydrogel" means a gel whose dispersing medium is water.

"Hydrophilic polymer" means a polymer that is capable of absorbing water or that is water-soluble.

The present invention relates to a self-foaming composition capable of forming a hydrogel foam in an acid medium.

The invention also relates to a method for preparing said composition and the use thereof as a drug for preventing and/or treating obesity.

The Composition

"Composition that is self-foaming in an acid medium" means, in the sense of the invention, a composition that is capable of forming a foam when it is introduced into, or brought into contact with, an aqueous medium having an acid pH, preferably a pH less than or equal to 5, better still from 0.5 to 5, advantageously from 1 to 5, and even more advantageously from 1 to 4. The foaming of said composition requires neither injection of gases nor application of mechanical stirring.

The present invention relates to a composition comprising:
  at least one hydrophilic polymer,
  at least one compound capable of crosslinking the hydrophilic polymer by forming ionic bonds,
  at least one foaming agent, and
  at least one foam stabilizer.

Preferably, the composition according to the invention comprises, or better still consists essentially of:
  from 0.1 to 50 wt % of hydrophilic polymer,
  from 0.01 to 50 wt % of compound capable of crosslinking the hydrophilic polymer by forming ionic bonds,
  from 0.01 to 50 wt % of foaming agent, and
  from 0.01 to 10 wt % of foam stabilizer,
  the percentages being expressed in dry matter relative to the total weight of dry matter in the composition.

More preferably, the composition according to the invention comprises, or better still consists essentially of:
  from 0.5 to 40 wt % of hydrophilic polymer,
  from 0.1 to 20 wt % of compound capable of crosslinking the hydrophilic polymer by forming ionic bonds,
  from 0.1 to 20 wt % of foaming agent, and
  from 0.05 to 5 wt % of foam stabilizer,
  the percentages being expressed in dry matter relative to the total weight of dry matter in the composition.

Even more preferably, the composition according to the invention comprises, or better still consists essentially of:
  from 0.5 to 20 wt % of hydrophilic polymer,
  from 0.5 to 15 wt % of compound capable of crosslinking the hydrophilic polymer by forming ionic bonds,
  from 0.5 to 15 wt % of foaming agent, and
  from 0.1 to 5 wt % of foam stabilizer,
  the percentages being expressed in dry matter relative to the total weight of dry matter in the composition.

Advantageously, the composition according to the invention comprises, or better still consists essentially of:
  from 0.5 to 15 wt % of hydrophilic polymer,
  from 0.5 to 10 wt % of compound capable of crosslinking the hydrophilic polymer by forming ionic bonds,
  from 0.5 to 10 wt % of foaming agent, and
  from 0.1 to 5 wt % of foam stabilizer,
  the percentages being expressed in dry matter relative to the total weight of dry matter in the composition.

More advantageously, the composition according to the invention comprises, or better still consists essentially of:
  from 0.5 to 10 wt % of hydrophilic polymer,
  from 0.5 to 5 wt % of compound capable of crosslinking the hydrophilic polymer by forming ionic bonds,
  from 0.5 to 5 wt % of foaming agent, and
  from 0.1 to 2.5 wt % of foam stabilizer,
  the percentages being expressed in dry matter relative to the total weight of dry matter in the composition.

Even more advantageously, the composition according to the invention comprises, or better still consists essentially of:
  from 0.5 to 5 wt % of hydrophilic polymer,
  from 0.5 to 2 wt % of compound capable of crosslinking the hydrophilic polymer by forming ionic bonds,
  from 0.5 to 2 wt % of foaming agent, and
  from 0.1 to 1 wt % of foam stabilizer,
  the percentages being expressed in dry matter relative to the total weight of dry matter in the composition.

The composition according to the invention comprises from 0.1 to 100 wt % of dry matter relative to the total weight of the composition, preferably from 1% to 50% and even more preferably from 2% to 20%, the remainder of the composition being water.

According to a first embodiment, the composition according to the invention is a hydrogel.

According to a second embodiment, the composition according to the invention may be dried in order to remove the water present in the hydrogel.

According to this second embodiment, the composition according to the invention is in the form of a xerogel, a cryogel or else an aerogel.

The Hydrophilic Polymer

The composition according to the invention comprises at least one hydrophilic polymer, i.e. a polymer that is capable of absorbing water or that is water-soluble. Advantageously, the hydrophilic polymer is water-soluble.

"Water-soluble polymer" means, in the sense of the invention, a polymer that has, at room temperature, a water solubility greater than or equal to 0.1 wt % relative to a given volume of water.

Preferably, the water-soluble polymer is a water-swelling polymer.

"Water-swelling polymer" means, in the sense of the invention, a polymer or copolymer capable of swelling by absorption of water.

The hydrophilic polymer used in the composition according to the invention is a polymer that is crosslinkable by the formation of ionic bonds.

Preferably, the hydrophilic polymer is suitable for being ingested by the oral route in humans and/or animals, notably in mammals.

Preferably, the hydrophilic polymer is a slightly calorigenic polymer, preferably noncalorigenic.

"Slightly calorigenic polymer" means, in the sense of the invention, a polymer that supplies few calories to the organism upon digestion thereof.

A slightly calorigenic hydrophilic polymer is particularly advantageous in the context of using a composition according to the invention as a drug for treating obesity, but also for preventing obesity in patients with diabetes.

Preferably, the hydrophilic polymer is selected from the anionic polymers.

Even more preferably, the hydrophilic polymer is selected from polysaccharides, polysaccharide derivatives and mixtures thereof.

"Polysaccharides and derivatives thereof" means, in the sense of the invention, polymers and copolymers consisting of several monosaccharide units and/or several units derived from monosaccharides and joined together by glycosidic bonds. The derived units may notably be selected from: monosaccharide units bearing a carboxylic acid and/or amine function and/or an alkyl amide group or else an ester function of an alkyl carboxylic acid.

For example, as polysaccharides and polysaccharide derivatives, we may notably mention alkyl celluloses such as $C_1$-$C_6$ alkyl celluloses and notably methyl cellulose, ethyl cellulose and ethyl methyl cellulose; substituted alkyl celluloses such as hydroxides of $C_1$-$C_6$ alkyl celluloses and the $C_1$-$C_6$ hydroxides of $C_1$-$C_6$ alkyl celluloses and notably n-propylcellulose hydroxide, hydroxypropylmethylcellulose, ethylhydroxyethylcellulose and carboxymethylcellulose; substituted dextrans such as dextran sulfate, dextran phosphate and diethylamine dextran; glycosaminoglycans and notably hyaluronic acid, chondroitin, and chondroitin sulfate; and polymers and copolymers comprising uronic acid units.

Preferably, the hydrophilic polymer is selected from carrageenan κ (kappa), carrageenan ι (iota), polysaccharides comprising uronic units and mixtures thereof, more preferably the hydrophilic polymer is selected from polysaccharides comprising uronic units.

"Uronic units" means, in the sense of the invention, polymer units derived from simple monosaccharides obtained by oxidation of the carbon located at the end of the chain to a carboxylic acid function.

Said uronic units are for example mannuronic acid, guluronic acid, glucuronic acid, iuduronic acid or galacturonic acid. The polymers and copolymers comprising uronic units are obtained by formation of glycosidic bonds with other monomers.

Preferably, at least 50% of the monosaccharide units of the hydrophilic polymer are uronic units, preferably at least 80%.

More preferably, the hydrophilic polymer consists essentially of uronic units.

According to a first embodiment, the hydrophilic polymer is selected from the polysaccharides consisting essentially of α-D-galacturonic units, preferably selected from pectins.

According to a second embodiment, the hydrophilic polymer is selected from the polymers comprising mannuronic units, derived from mannuronic acid of formula (I), and guluronic units, derived from guluronic acid of formula (II).

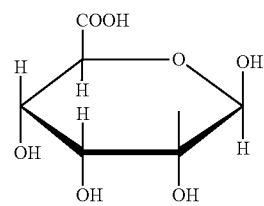

(I)

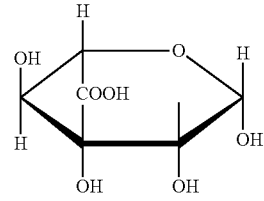

(II)

Preferably, according to this embodiment, the hydrophilic polymer is selected from alginates.

"Alginates" means, in the sense of the invention, random or block polymers of formula (III) consisting essentially of mannuronic units and guluronic units. The polymer of formula (III) consists of m mannuronic units and n guluronic units, m and n being two integers.

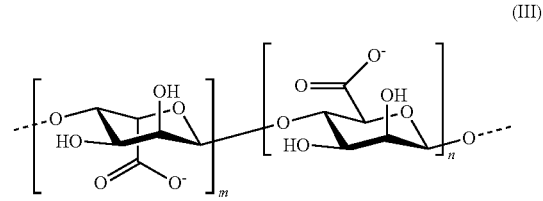

(III)

Preferably, at least 15 wt % of the alginate consists of chain segments on which two guluronic units follow one another directly, preferably at least 25 wt % and even more preferably at least 50 wt %.

Preferably, the hydrophilic polymer of the invention has a weight-average molecular weight from 10 000 g/mol to 500 000 g/mol, preferably from 30 000 g/mol to 200 000 g/mol, and even more preferably from 50 000 g/mol to 100 000 g/mol.

According to a first embodiment, the hydrophilic polymer is partially crosslinked before being introduced into the composition.

The hydrophilic polymer may be partially crosslinked by the formation of ionic bonds (partial physical crosslinking) or partially crosslinked by the formation of covalent bonds (partial chemical crosslinking) or else partially crosslinked by the formation of ionic bonds and covalent bonds (partial mixed crosslinking).

Preferably, and according to this same embodiment, the hydrophilic polymer is crosslinked by the formation of ionic bonds (partial physical crosslinking) before being introduced into the composition.

According to this same embodiment, the hydrophilic polymer has a crosslinking index less than or equal to 50%, preferably less than or equal to 30%, even more preferably less than or equal to 10%, before it is introduced into the composition.

"Crosslinking index" means, in the sense of the invention, the ratio of the number of crosslinking sites occupied by a polymer chain to the number of possible crosslinking sites on this same polymer.

The crosslinking index is calculated taking into account the nature and the quantity of monomers and crosslinking agents used.

According to this first embodiment, advantageously the hydrophilic polymer is partially crosslinked by the formation of ionic bonds.

According to a second preferred embodiment, the hydrophilic polymer is not crosslinked.

Advantageously, the composition according to the invention has a content of hydrophilic polymer from 10 to 99.5 wt % relative to the total weight of the composition, preferably from 15% to 99%, and even more preferably from 15% to 80%, the percentages being expressed in weight of dry matter.

The Compound Capable of Crosslinking the Hydrophilic Polymer by Forming Ionic Bonds The composition according to the invention comprises at least one compound capable of crosslinking the hydrophilic polymer by forming ionic bonds.

In the case when the hydrophilic polymer is selected from anionic polymers, the compound capable of crosslinking the hydrophilic polymer by forming ionic bonds is selected from divalent cations, trivalent cations and mixtures thereof.

Among the divalent cations suitable for the invention, we may mention: calcium(II), manganese(II), silver(II), iron (II), copper(II), magnesium(II), and mixtures thereof.

Depending on the chemical nature of the cation used, the hydrogel obtained by crosslinking of hydrophilic polymer will have different physical properties, notably a different stability.

In particular, a hydrogel obtained by crosslinking the hydrophilic polymer with magnesium ions will be relatively more fragile mechanically and will have a more limited life, compared to the hydrogels obtained from other cations.

Conversely, a hydrogel obtained by crosslinking the hydrophilic polymer with calcium ions will be mechanically stable for a long time.

The choice of cation therefore makes it possible to modulate the life of the crosslinked gel in the stomach of an individual who has ingested the composition.

Preferably, the divalent cation is calcium.

Among the trivalent cations suitable for the invention, we may mention: aluminum, iron(III) and mixtures thereof.

Preferably, the compound capable of crosslinking the hydrophilic polymer by forming ionic bonds is selected from divalent cations.

More preferably, the cation is calcium.

Crosslinking of the anionic hydrophilic polymer by the formation of ionic bonds is advantageous in that it is reversible.

For example, when the compound capable of crosslinking the hydrophilic polymer by forming ionic bonds is selected from divalent and/or trivalent cations, crosslinking is reversible. Reversibility is obtained by adding an excess of monovalent cations, for example selected from sodium, potassium and mixtures thereof.

We may also mention compounds of the acid type, and notably compounds of the acid type that can be ingested, which, once in contact with the hydrogel, chelate the divalent and/or trivalent cations and facilitate exchange of the divalent and/or trivalent cations with monovalent cations.

For example, as compounds of the acid type capable of chelating the divalent and trivalent cations, we may mention citric acid or ascorbic acid.

Advantageously, the compound capable of crosslinking the hydrophilic polymer by forming ionic bonds is introduced into the composition according to the invention in the form of a salt of a divalent or trivalent cation and of a counter-ion.

According to the invention, the compound capable of crosslinking the hydrophilic polymer by forming ionic bonds is introduced into the composition in an inactive form.

"Inactive form" means, in the sense of the invention, that in aqueous solution and at neutral pH and notably at pH from 6.5 to 7.5 said compound capable of crosslinking the hydrophilic polymer does not dissociate. More particularly, at neutral pH, notably at pH from 6.5 to 7.5, crosslinking of the hydrophilic polymer by this compound does not take place.

By passage in an acid medium and notably in aqueous solution at pH less than or equal to 6.5, preferably less than or equal to 6 and even more preferably at pH less than or equal to 5, the compound dissociates and releases chemical species capable of crosslinking the hydrophilic polymer by forming ionic bonds.

When the compound capable of crosslinking the hydrophilic polymer by forming ionic bonds is selected from divalent and/or trivalent cations, it is preferably introduced into the composition according to the invention in the form of a metal salt.

More particularly, the metal salt is preferably selected from the salts of divalent cations, the salts of trivalent cations and mixtures thereof.

More preferably, the metal salt is selected from salts capable of decomposing in an aqueous medium on the one hand into divalent and/or trivalent cations and on the other hand into an acid-base species, in the Brønsted sense.

The acid-base species, in the Brønsted sense, released by the decomposition of the metal salt in an aqueous medium preferably has a pKa less than or equal to 7, preferably less than or equal to 6.5.

According to a preferred embodiment, the acid-base species released by the decomposition of the metal salt in an aqueous medium is selected from the hydrogen carbonate or bicarbonate ion $HCO_3^-$, the carbonate ion $CO_3^{2-}$ and mixtures thereof. By lowering the pH, notably to pH less than or equal to 6, these hydrogen carbonate or bicarbonate ions $HCO_3^-$ and/or carbonate ions $CO_3^{2-}$ are transformed into carbonic acid $H_2CO_3$, which decomposes into carbon dioxide $CO_2$.

Preferably, the metal salt is selected from salts that are insoluble in water at room temperature and at neutral pH, notably at a pH from 6.5 to 7.5.

More preferably, the metal salt has a water solubility at neutral pH, notably at a pH from 6.5 to 7.5, determined at 20° C., less than or equal to 0.5 g/L, even more preferably less than 0.1 g/L.

According to a preferred embodiment, the metal salt is selected from salts:
   that decompose in an aqueous medium on the one hand into divalent and/or trivalent cations and on the other hand into an acid-base species, in the Brønsted sense, and
   that have a water solubility at neutral pH, notably at a pH from 6.5 to 7.5, determined at 20° C., less than or equal to 0.5 g/L, more preferably less than 0.1 g/L.

This preferred embodiment is advantageous in that the metal salt is water-insoluble at neutral pH and remains in the inactive form. However, passage in an acid medium, notably at a pH below the pKa of the acid/base pair defined above, causes dissolution of the metal salt, thus allowing release of the divalent or trivalent cations and availability thereof for ionic crosslinking of the hydrophilic polymer.

More preferably, this metal salt has a pKa less than or equal to 7, preferably less than or equal to 6.5, more preferably less than or equal to 6, and advantageously less than or equal to 5.

More particularly, when the compound capable of crosslinking the hydrophilic polymer by forming ionic bonds is selected from divalent cations, the metal salt is advantageously selected from calcium carbonate $CaCO_3$, manganese carbonate $MnCO_3$, silver carbonate $AgCO_3$, iron carbonate $FeCO_3$, copper carbonate $CuCO_3$, magnesium carbonate $MgCO_3$, hydroxyapatite $Ca_{10}(PO_4)_6OH_2$ and mixtures thereof.

Advantageously, when the compound capable of crosslinking the hydrophilic polymer by forming ionic bonds is selected from divalent cations, it is introduced into the composition according to the invention in the form of one or more carbonate salts and a divalent metal cation.

When the compound capable of crosslinking the hydrophilic polymer by forming ionic bonds is selected from trivalent cations, the metal salt is advantageously selected from salts of aluminum $Al^{3+}$, for example aluminum carbonate $Al_2(CO_3)_3$, ferric salts $Fe^{3+}$, and mixtures thereof.

Advantageously, the metal salt is selected from metal salts that can be ingested by humans and/or animals and notably by mammals.

As metal salts that can be ingested by humans and/or animals, we may notably mention calcium carbonate $CaCO_3$, magnesium carbonate $MgCO_3$, hydroxyapatite $Ca_{10}(PO_4)_6OH_2$, iron carbonate $FeCO_3$, aluminum carbonate $Al_2(CO_3)_3$ and mixtures thereof.

Advantageously, the compound capable of crosslinking the hydrophilic polymer by forming ionic bonds is introduced into the composition according to the invention in the form of a salt of a divalent metal cation, more preferably in the form of a carbonate salt and a divalent metal cation.

Preferably, the metal salt is calcium carbonate $CaCO_3$.

The carbonate salts and notably calcium carbonate are advantageous in that they contribute to gas release and therefore to the formation of foam. They are also advantageous in that they do not leave any residue in the stomach: most of the cations and gas released contribute to formation of the foam.

According to an alternative embodiment, the counter-ion of the compound capable of crosslinking the hydrophilic polymer by forming ionic bonds is selected from a nutritional substance, for example such as a vitamin.

The compound capable of crosslinking the hydrophilic polymer by forming ionic bonds is advantageously introduced into the composition in an amount such that the crosslinked polymer, after passage in an acid medium, notably at a pH less than or equal to 5, preferably from 0.5 to 5, even more preferably from 1 to 5, and advantageously from 1 to 4, has a degree of crosslinking less than or equal to 100%, preferably less than or equal to 95%, and even more preferably less than or equal to 90%.

The compound capable of crosslinking the hydrophilic polymer by forming ionic bonds is advantageously introduced into the composition in an amount such that the crosslinked polymer, after passage in an acid medium, notably at a pH less than or equal to 5, preferably from 0.5 to 5, even more preferably from 1 to 5, and advantageously from 1 to 4, has a degree of crosslinking greater than or equal to 5%, preferably greater than or equal to 10%, even more preferably greater than or equal to 15%, and advantageously greater than or equal to 20%.

A degree of crosslinking that is too low is not suitable for the present invention, as it would not allow formation of a foam with adequate mechanical stability.

More particularly, if the hydrophilic polymer is not sufficiently crosslinked, the gas produced in the hydrogel by the decomposition of the foaming agent cannot be retained sufficiently by the gelled structure, the gas escapes and the foam structure does not form or is of a too ephemeral nature to act upon the sensation of satiety.

The Foaming Agent

The composition according to the invention comprises at least one foaming agent.

The foaming agent is defined in the invention as any substance or combination of substances capable of producing or of decomposing/dissociating into gas under the action of an environmental factor or of a chemical compound.

Advantageously, the foaming agent is different from the compound capable of crosslinking the hydrophilic polymer by forming ionic bonds.

Preferably, the foaming agent used in the composition according to the invention is a chemical foaming agent.

The chemical foaming agents comprise compounds having the property of reacting or of decomposing to form a gas when they are exposed to a reagent or to particular environmental conditions (temperature, pH, etc.).

The foaming agent is advantageously introduced into the composition according to the invention in an inactive form.

"Inactive form" means, in the sense of the invention, that in aqueous solution at neutral pH and notably at a pH from 6.5 to 7.5 and at room temperature, the foaming agent does not decompose and more particularly does not decompose into gas.

Advantageously, decomposition of the foaming agent into gas is initiated by passage in an acid medium, preferably at a pH less than or equal to 5, more preferably from 0.5 to 5, even more preferably from 1 to 5, and advantageously from 1 to 4.

Placed in an acid medium, the foaming agent decomposes into gas, preferably into carbon dioxide $CO_2$.

Advantageously, decomposition of the foaming agent into gas is initiated at pH less than or equal to 6.5, preferably less than or equal to 6, and more preferably at pH less than or equal to 5.

Preferably, the foaming agent is introduced into the composition according to the invention in the form of a salt, preferably in the form of a metal salt.

The salt is preferably selected from salts of monovalent cations, even more preferably from salts of monovalent metal cations, advantageously from salts of alkali metal cations.

More preferably, the salt is selected from salts capable of decomposing in an aqueous medium and at neutral pH, notably at a pH from 6.5 to 7.5, on the one hand into monovalent cations and on the other hand into an acid-base species, in the Brønsted sense.

Advantageously, the acid-base species, in the Brønsted sense, released by the decomposition of the salt in an aqueous medium has a pKa less than or equal to 7, preferably less than or equal to 6.5.

Through passage in an acid medium, notably at a pH below the pKa defined above, the acid-base species released by the decomposition of the salt in an aqueous medium reacts to form the conjugated Brønsted acid.

The conjugated Brønsted acid is preferably selected from compounds capable of decomposing into gas, more preferably into carbon dioxide $CO_2$.

According to a preferred embodiment, the acid-base species released by the decomposition of the salt in an aqueous medium is selected from the hydrogen carbonate or bicarbonate ion $HCO_3^-$, the carbonate ion $CO_3^{2-}$ and mixtures thereof. The conjugated Brønsted acid is then carbonic acid $H_2CO_3$, which decomposes into carbon dioxide $CO_2$.

More preferably, the salt, preferably the metal salt, is selected from salts having a pKa less than or equal to 7, preferably less than or equal to 6.5, more preferably less than or equal to 6, and advantageously less than or equal to 5.

The salt is preferably selected from the carbonates and bicarbonates of monovalent cations, alone or mixed, preferably from the carbonates and bicarbonates of alkali metal cations.

Even more preferably, the salt is selected from sodium carbonate $Na_2CO_3$, sodium bicarbonate $NaHCO_3$, ammonium bicarbonate $NH_4CO_3$, potassium bicarbonate $KHCO_3$ and mixtures thereof.

Placed in an aqueous medium and at neutral pH, notably at a pH from 6.5 to 7.5, the aforementioned salts decompose into monovalent cations ($Na^+$, $NH_4^+$ or $K_+$) and bicarbonate ions $HCO_3^-$. Through passage in an acid medium, notably at a pH less than or equal to 5, preferably from 0.5 to 5, more preferably from 1 to 5 and advantageously from 1 to 4, the bicarbonate ions $HCO_3^-$ react to form carbonic acid $H_2CO_3$, which then decomposes into carbon dioxide $CO_2$.

Advantageously, the salt is selected from salts that can be ingested by humans and animals and notably by mammals.

As salts that can be ingested by humans and animals and notably by mammals, we may mention: sodium carbonate $Na_2CO_3$, sodium bicarbonate $NaHCO_3$, ammonium bicarbonate $NH_4CO_3$, potassium bicarbonate $KHCO_3$ and mixtures thereof.

Advantageously, the salt is selected from salts of monovalent metal cations, more advantageously from sodium carbonate $Na_2CO_3$, sodium bicarbonate $NaHCO_3$, potassium bicarbonate $KHCO_3$ and mixtures thereof.

More advantageously, the salt is selected from salts of bicarbonate and of monovalent metal cations.

Preferably, the salt is sodium bicarbonate $NaHCO_3$.

The amount of foaming agent introduced into the composition according to the invention is determined relative to the amount of compound capable of crosslinking the hydrophilic polymer by forming ionic bonds introduced into the same composition. The amount of foaming agent is notably determined taking into account the possible contribution of the compound capable of crosslinking the hydrophilic polymer by forming ionic bonds to the release of gas and therefore to formation of the foam.

According to a particular embodiment of the invention, the foaming agent is selected from the metal salts that decompose into monovalent cations, and the compound capable of crosslinking the hydrophilic polymer by forming ionic bonds is selected from divalent and/or trivalent cations.

Preferably, when the foaming agent is a metal salt that decomposes into monovalent cations, it is introduced into the composition according to the invention in an amount such that the ratio of the quantity of divalent and/or trivalent cations to the quantity of monovalent cations introduced into the composition is greater than or equal to 0.05, preferably greater than or equal to 0.5, the quantities of cations being expressed in moles.

Thus, according to this embodiment, the monovalent cation released by the foaming agent is present in proportions such that it does not compete with the divalent and/or trivalent cations, notably divalent, responsible for the crosslinking of the hydrophilic polymer to the point of significantly degrading the crosslinking of the hydrophilic polymer.

More preferably, when the foaming agent is a metal salt that decomposes into monovalent cations, it is introduced into the composition according to the invention in an amount such that the ratio of the quantity of divalent cations to the quantity of monovalent cations introduced into the composition is greater than or equal to 0.05, preferably greater than or equal to 0.5, the quantities of cations being expressed in moles.

According to a preferred embodiment, the compound capable of crosslinking the hydrophilic polymer by forming ionic bonds is introduced into the composition according to the invention in the form of calcium carbonate and the foaming agent is sodium bicarbonate.

More preferably, according to this preferred embodiment, calcium carbonate and sodium bicarbonate are introduced into the composition according to the invention in a molar ratio from 1:1 to 1:10, preferably from 1:1 to 1:5.

The release of gas in the polymer matrix makes it possible to obtain a large number of cells, mostly connected, to form an open-cell foam.

The amount of gas trapped in the matrix depends on the viscosity of the medium before crosslinking, on the amount of crosslinking agent and therefore on the degree of crosslinking, the amount and type of foaming agent introduced into the matrix, and the amount and nature of the foam stabilizer.

In the context of this invention, release of gas and crosslinking of the hydrophilic polymer are carried out simultaneously so as to trap the gas formed inside the polymer matrix and allow formation of a foam, in particular a stable foam.

The Foam Stabilizer

The composition according to the invention comprises at least one foam stabilizer.

"Foam stabilizer" means, in the sense of the invention, a compound capable of lowering the surface tension at the interface of two different media and notably at the interface separating a liquid medium from a gaseous medium.

Preferably, the foam stabilizer is selected from structure-forming agents, surfactants and mixtures thereof.

The Structure-Forming Agents

"Structure-forming agent" means, in the sense of the invention, a chemical compound capable of stabilizing the structure of a foam.

The structure-forming agents are classified into 2 categories depending on their chemical nature:
peptides and proteins, and
saccharides.

Preferably, the structure-forming agent is selected from peptides and proteins.

Peptides and Proteins

"Peptide or protein" means, in the sense of the invention, a chain of several amino acids joined together by peptide bonds.

More particularly, the term "peptide" is used when the number of amino acids present in the chain is less than 50.

The term "protein" is used when the number of amino acids present in the chain is greater than or equal to 50.

Preferably, the structure-forming agent is selected from proteins.

Even more preferably, the protein is selected from gelatins, albumin, ovalbumin, milk casein, lecithin, the salts thereof for example such as sodium caseinate, and mixtures thereof.

Saccharides

"Saccharides" means, in the sense of the invention, organic compounds comprising one or more simple monosaccharides.

Preferably, foam stabilizer saccharides are selected from xanthan gum, glucomannan gum, gum arabic, carob gum and mixtures thereof.

Surfactants

"Surfactant" means, in the sense of the invention, an amphiphilic compound comprising a hydrophobic moiety, notably a long carbon chain, and a hydrophilic moiety.

Surfactants are classified in 4 categories depending on the nature of the hydrophilic group:
  anionic surfactants,
  cationic surfactants,
  zwitterionic or amphoteric surfactants, and
  nonionic surfactants.

Preferably, the surfactant is selected from amphoteric surfactants and nonionic surfactants.

Zwitterionic or Amphoteric Surfactants

"Zwitterionic or amphoteric surfactant" means, in the sense of the invention, a surfactant whose hydrophilic moiety consists of an acid-base group.

In an acid medium, the hydrophilic group is positively charged.

In a basic medium, the hydrophilic group is negatively charged.

Among the zwitterionic or amphoteric surfactants suitable for the invention, we may notably mention betaines, imidazoline derivatives, phospholipids and mixtures thereof.

"Phospholipid" means, in the sense of the invention, a lipid containing at least one phosphoric acid function. The phospholipids notably include phosphatic acids and phosphoglycerides.

Nonionic Surfactants

"Nonionic surfactant" means, in the sense of the invention, a surfactant in which the hydrophilic moiety is not charged.

Among the nonionic surfactants we may mention for example: polymers and copolymers of ethylene glycol and propylene glycol, fatty acid esters and (poly)ethylene oxide esters, ethers of fatty alcohols and of (poly)ethylene oxide, ethers of (poly)ethoxylated polyols, esters of fatty acid and polyols notably the esters of fatty acid and sugars, optionally (poly)ethoxylated, fatty acid glycerides, ethoxylated glycerol ethers, ethers of glycerol and fatty alcohols, fatty acids.

"Fatty acid" means, in the sense of the invention, a compound of the carboxylic acid type comprising a hydrocarbon-containing linear chain of 10 to 30 carbon atoms.

"Ethoxylated" means, in the sense of the invention, a chemical compound that has undergone a step of ethoxylation by reaction with ethylene oxide.

According to a first embodiment, the nonionic surfactant is selected from the hydrocarbons of poly(ethylene oxide), preferably selected from the ethers and esters of polyoxyethylene glycol, the esters of fatty acid and polyols, the esters of fatty acids and of ethoxylated polyols and mixtures thereof.

For example, the nonionic surfactant may be selected from ethoxylated sorbitans, ethoxylated isosorbides, esters of fatty acids and ethoxylated sorbitans, esters of fatty acids and ethoxylated isosorbides, esters of fatty acids and sorbitans, esters of fatty acids and isosorbides, and mixtures thereof.

Among the esters of fatty acids and sorbitans, we may notably mention the commercial products SPAN®, for example SPAN®20, SPAN®40 or SPAN®80 marketed by Croda Inc.

Among the esters of fatty acids and ethoxylated sorbitans, we may notably mention the commercial products Tween®, for example Tween®20, Tween®60 or Tween®80 marketed by Croda Inc.

According to a second embodiment, the nonionic surfactant is selected from the fatty acids, and even more preferably is linoleic acid.

According to one embodiment, the foam stabilizer may be a mixture of various stabilizers and/or of various surfactants.

Advantageously, the composition according to the invention has a content of foam stabilizer from 0.01 to 5 wt % relative to the total weight of the composition, preferably from 0.05 to 2 wt % and even more preferably from 0.1 to 1 wt %, the percentages being expressed in weight of dry matter.

Other Additives

The composition according to the invention may comprise a second water-swelling polymer.

This second water-swelling polymer differs from the hydrophilic polymer described above in that it is not crosslinkable by the formation of ionic bonds.

The presence of a second water-swelling polymer in the compositions according to the invention is advantageous in that it makes it possible to obtain foams of larger volume, thus increasing the degree of swelling of the composition.

Preferably, the water-swelling polymer that cannot be crosslinked by the formation of ionic bonds is selected from starch, agar-agar, carrageenan λ(lambda), the noncrosslinkable celluloses and mixtures thereof.

More preferably, the water-swelling polymer can be ingested by humans and animals and notably mammals.

As water-swelling polymers that can be ingested by humans and animals and notably mammals, we may mention agar-agar, carrageenan λ(lambda), the noncrosslinkable celluloses and mixtures thereof.

Advantageously, the composition according to the invention has a content of water-swelling polymer from 0 to 50 wt % relative to the total weight of the composition, preferably from 1% to 30% and even more preferably from 5% to 20%, the percentages being expressed in weight of dry matter.

The composition according to the invention may further comprise, nonexhaustively, additives selected from: dyes, flavorings, vitamins, dietary fiber.

According to a certain embodiment, the composition according to the invention further comprises a palatability product in the form of a mixture of at least one flavoring and at least one flavor enhancer.

Flavorings are classified in two categories:
  flavorings of natural origin, obtained from material of vegetable origin,
  artificial or synthetic flavorings, obtained by synthesis in the laboratory.

Among the natural flavorings, we may mention limonene or citral, obtained by extraction from the peel of citrus fruits such as oranges and lemons.

Among the artificial or synthetic flavorings, we may mention vanillin or 3-methoxy-4-hydroxybenzaldehyde, ethyl vanillin or 3-ethyl-4-hydroxybenzaldehyde.

For a composition intended to be ingested by an animal, and notably a mammal, we may also mention recycled vegetable or animal oils, wastes from food industries and restaurants, hydrolyzates of poultry livers or the products from the fermentation of fish.

"Flavor enhancer" means, in the sense of the invention, a chemical that makes it possible to increase the intensity of the olfactory/gustatory perception of a portion of food. An enhancer does not have a particular flavor and does not alter the taste of foodstuffs, it merely intensifies the taste of foodstuffs.

As flavor enhancers, we may notably mention sodium glutamate, guanylates, inosinates, ribonucleotides, glycine, zinc acetate, trisodium pyrophosphate, phyllosilicates or glucomannans.

For example, for a composition intended to be ingested by humans, the flavor enhancer may be selected from sodium glutamate, guanylates, inosinates, ribonucleotides, glycine and zinc acetate.

For example, for a composition intended to be ingested by an animal, and notably by a mammal, the flavor enhancer may be selected from trisodium pyrophosphate, phyllosilicates or glucomannans.

According to this embodiment, the composition according to the invention preferably comprises 0.1 to 5 wt % of palatability agents, preferably from 1 to 5 wt %, the percentages being expressed in weight of dry matter.

Method of Manufacture

The invention also relates to a method for preparing a composition according to the invention.

The method according to the invention comprises introducing the following into an aqueous medium, in particular into water:
the hydrophilic polymer,
the foaming agent,
the compound capable of crosslinking the hydrophilic polymer by forming ionic bonds, and
the foam stabilizer.

The aqueous medium is preferably at neutral pH, notably at a pH from 6.5 to 7.5.

The compounds defined above may be introduced into the aqueous medium in any order and the order of introduction does not generally have any effect on the final composition. The compounds defined above may thus be introduced into the aqueous medium simultaneously or by successive additions.

When they are introduced in successive steps, they may be added to the aqueous medium in any order.

According to a first variant, the method according to the invention comprises the following steps:
(1) dissolving or dispersing the hydrophilic polymer in water, preferably at neutral pH, more preferably at a pH from 6.5 to 7.5, with stirring,
(2) with stirring, dispersing the foaming agent and the compound capable of crosslinking the hydrophilic polymer by forming ionic bonds until a homogeneous dispersion is obtained,
(3) adding the foam stabilizer.

According to a second variant, the method according to the invention comprises the following steps:
(1') dissolving or dispersing the foam stabilizer in water, preferably at neutral pH, more preferably at a pH from 6.5 to 7.5, with stirring,
(2') introducing the following into the medium resulting from (1'), preferably with stirring:
the hydrophilic polymer,
the foaming agent, and
the compound capable of crosslinking the hydrophilic polymer by forming ionic bonds.

This second variant is particularly suitable when the foam stabilizer is in the form of a solid and consequently requires a preliminary step of dissolution and/or dispersion. A foam stabilizer of this kind in solid form is for example gelatin.

According to a first embodiment, the composition is obtained directly at the end of the preceding process. In this case, the composition is obtained in the form of an aqueous dispersion.

According to a second embodiment, the method may further comprise an additional step of drying, notably after step (3) or (2').

This additional drying step is carried out so as to remove, wholly or partly, the water present in the composition.

Preferably, the step of drying the composition is carried out by pulsed hot air injection, by treatment with supercritical carbon dioxide $CO_2$, by lyophilization or by atomization, even more preferably by treatment with supercritical carbon dioxide $CO_2$.

When drying of the composition is carried out by treatment with supercritical carbon dioxide $CO_2$, the latter requires a preliminary step of solvent exchange, during which the water of the composition is replaced with a more volatile solvent of the alcohol type.

The method according to the invention therefore makes it possible to obtain compositions with a controlled water content, as a function of the duration and intensity of the drying applied.

In particular, in the absence of an additional drying step, the method according to the invention makes it possible to prepare a composition in the form of an aqueous dispersion.

Conversely, by total drying of the composition, the method makes it possible to prepare a water-free composition, in the form of a xerogel, a cryogel or an aerogel depending on the manner of drying used.

More particularly, when the composition is dried completely by pulsed hot air injection, the composition is obtained in the form of a xerogel.

When the composition is dried completely by treatment with supercritical carbon dioxide $CO_2$, the composition is obtained in the form of an aerogel.

When the composition is dried completely by lyophilization, the composition is obtained in the form of a cryogel.

By partial drying, the method according to the invention makes it possible to obtain compositions of varied consistency: in solid or liquid forms, viscous or fluid, and notably in the form of syrups.

In particular, by total or partial drying, the method according to the invention makes it possible to prepare compositions in the form of powders.

Preferably, the powders obtained by drying a composition according to the invention have a granulometry less than or equal to 2 mm, preferably less than or equal to 1 mm, even more preferably less than or equal to 0.8 mm.

The granulometry of the powders is measured using a LASER Mastersizer 3000® granulometer marketed by the company Malvern. It is equipped with a high-energy (HE) venturi, a grating placed on the sieve with an aperture of 5 mm and beads of 10 mm facilitating passage of the sample through this grating.

2 g to 10 g of powder is introduced into the hopper with a selected aperture of 2 mm, a degree of vibration of the hopper at 30-40%, a pressure ranging from 2 to 4 bar and an obscuration ranging from 2 to 15% depending on the amount of material. Between 5 and 10 measurements are carried out per sample.

The average diameter of a sphere of equivalent volume is then determined by measuring the average diameter of the most representative class (Gaussian maximum) by volume, regarded as the average diameter of the particles under investigation.

Uses

The invention also relates to a composition according to the invention for use as a drug, in particular for preventing and/or treating obesity.

The composition according to the invention is notably intended to be ingested by humans or animals and notably by mammals in order to produce an "appetite suppressing" effect in the patient, linked to the development of a sensation of satiety.

This sensation of satiety in the patient, human or animal, is obtained by swelling of the composition at the level of the stomach, thus causing a reduction of the gastric volume.

The composition according to the invention is a composition that is self-foaming in an acid medium, preferably at a pH less than or equal to 5, more preferably from 0.5 to 5, even more preferably from 1 to 5, and advantageously from 1 to 4.

"Composition that is self-foaming in an acid medium" means, in the sense of the invention, a composition capable of expanding in the form of a foam when it is placed in an acid medium, preferably at a pH less than or equal to 5, better still from 0.5 to 5, advantageously from 1 to 5, and even more advantageously from 1 to 4. In particular, foaming of a self-foaming composition according to the invention requires neither injection of gases nor application of mechanical stirring.

Preferably, the composition according to the invention forms a foam when it is placed in an aqueous medium at a pH less than or equal to 6, preferably less than or equal to 5, even more preferably less than or equal to 4.

Preferably, the composition according to the invention forms a foam when it is placed in an aqueous medium at a pH greater than or equal to 0.5, preferably greater than or equal to 1.

Thus, placed in an acid medium, notably in the stomach, the composition according to the invention expands and swells so as to form a foam.

Just before eating a meal, the stomach pH is typically between 0.5 and 2.5. As a meal is eaten, the pH gradually increases, reaching a value from 4 to 5 at the end of the meal.

At a pH from 4 to 5, the degree of swelling and the kinetics of swelling of the compositions according to the invention are significantly reduced.

The composition according to the invention is thus advantageous in that it makes it possible to avoid possible problems connected with ingestion of a composition according to the invention at the end of the meal, in contrast to the recommended protocols of use. In particular, ingestion of a composition according to the invention at the end of the meal is unlikely to lead to excessive swelling of the stomach of a patient who has already ingested a portion of food.

Swelling of the composition in an acid medium is made possible by two phenomena: foaming resulting from decomposition of the foaming agent into gas, and crosslinking of the polymer matrix, these two phenomena occurring simultaneously.

Placed in an acid medium, the composition according to the invention advantageously makes it possible to obtain a closed-cell foam.

"Closed-cell foam" means, in the sense of the invention, a foam having:
  a structure with closed cells, or
  a structure with open cells but provided with a closed external envelope.

A closed-cell foam is advantageous in that the gas responsible for its formation remains trapped inside the structure. In particular, in the context of the compositions according to the invention, the gas released during foaming of the composition remains trapped within the polymer matrix, thus preventing release of gases in the stomach.

A test for determining the closed or open character of a foam may consist for example of:
  1) drying the foam to be investigated,
  2) weighing the dried foam; this weight in dry form is designated $m_0$,
  2) placing the dry foam in an aqueous medium for 10 minutes,
  3) removing the foam from the aqueous medium and weighing it directly after removal from the aqueous medium so as to avoid the drying effects. This weight is designated $m_1$.
  4) calculating the degree of hydration of the foam DH, expressed as a percentage, by applying the following formula: $DH=[(m_0-m_1/m_0]*100$.

If the degree of hydration of the foam DH is less than or equal to 30%, the foam is said to be closed. Otherwise the foam has an open structure.

The foam obtained by swelling of the composition according to the invention preferably has a degree of hydration as defined above less than or equal to 20%, more preferably less than or equal to 15%.

It is found advantageously that the hydrophilic polymer present in the composition according to the invention then constitutes a continuous phase within the foam structure and forms a three-dimensional network.

It is found advantageously that the water-swelling polymer, noncrosslinkable by the formation of ionic bonds, forms a dispersed phase within the foam structure.

It is found advantageously that the foam stabilizer is located at the interface between the hydrophilic polymer and the gas bubbles trapped in the structure.

The formation of a foam is made possible by the decomposition of the foaming agent initiated by the passage in an acid medium. If applicable, the compound capable of crosslinking the hydrophilic polymer by forming ionic bonds also contributes to gas release and formation of a foam.

The crosslinking of the polymer matrix is made possible by the decomposition of the compound capable of crosslinking the hydrophilic polymer by forming ionic bonds caused by the passage in an acid medium.

The swelling of the composition is measured by the degree of swelling.

The degree of swelling is defined as the ratio of the difference between the volume of the composition expanded after foaming and the volume of the initial composition, to the volume of the initial composition.

The degree of swelling is measured as follows:

2 mL of a composition according to the invention is placed in a class A measuring cylinder graduated from 0 to 100 mL. 50 mL of an aqueous solution whose pH has been fixed by adding citric acid is then carefully introduced into the class A measuring cylinder graduated from 0 to 100 mL. It is important for the aqueous solution to be introduced carefully into the graduated measuring cylinder so as to be able to monitor the variation of the volume of the system.

The volume of the hydrogel is recorded at regular intervals using a chronometer, between 10 s and 1 min depending on the measurement conditions.

The swelling of the self-swelling hydrogel is monitored until the volume stabilizes and reaches a plateau. The volume corresponding to this plateau is regarded as the maximum swelling of the hydrogel in the conditions investigated. The degree of swelling of the self-swelling hydrogels is determined from the following equation:

$$G=(Vt-Vi)/Vi$$

with:

G: degree of swelling (without units)

Vt: volume determined at time t (in mL)

Vi: initial volume of the composition after drying (in mL)

The initial volume of the composition after drying Vi is determined as follows: 2 mL of the initial composition is poured into an aluminum dish with a diameter of 2 cm and is placed in an oven at 70° C. for 12 h. The dry product is then in the form of a disk with a diameter of 2 cm, the thickness of which is measured using a micrometer caliper gauge. The volume of this disk represents the initial volume of the composition after drying.

All the measurements are repeated 3 times to determine an average degree of swelling.

The composition according to the invention advantageously has a degree of swelling greater than or equal to 200, preferably greater than or equal to 250, even more preferably greater than or equal to 300.

The composition according to the invention preferably has a degree of swelling less than or equal to 500, preferably less than or equal to 400.

Owing to the presence of a foam stabilizer, the composition according to the invention in its expanded form, obtained by passage in an acid medium, is mechanically stable.

Crosslinking of the polymer matrix by the formation of ionic bonds is advantageous in that the crosslinked foam structure is reversible.

In particular, crosslinking is reversible under the action of monovalent cations in large excess. For example, the crosslinked foam structure can be broken down by ingesting monovalent metal salts, for example such as sodium chloride NaCl.

Moreover, the polymer chains, in particular the chains of polysaccharides or of polysaccharide derivatives, are hydrolyzable by the action of the gastric enzymes.

As a result, the composition according to the invention is easily digestible and can be eliminated by the organism via the usual mechanisms of digestion.

According to the invention, swelling of the composition is initiated by passage in the gastric environment, whereas the composition does not expand in the oral cavity and as it passes through the esophagus.

Thus, after being ingested and after reaching the stomach, the composition according to the invention expands.

When the patient ingests a composition according to the invention at the beginning of a meal, the volume available in the stomach is reduced on account of the expansion of the composition. This decrease in gastric volume has the effect that the patient will have to ingest a smaller amount of food than when the composition according to the invention has not been ingested, to attain a sensation of satiety.

By adding a foam stabilizer, it is possible to obtain a mechanically stable foam for a period of some hours, corresponding to the time interval between two successive meals.

The mechanical stability of the foam may for example be observed visually. It is then considered that a foam is mechanically stable if its degree of swelling does not decrease after swelling for 10 minutes, preferably after swelling for 15 minutes.

Formulation

The composition according to the invention is intended to be ingested by humans and/or animals and notably by mammals.

According to a first embodiment, the composition according to the invention may be ingested in the form of a solid and notably in the form of powders, coated or uncoated tablets, or granules.

According to a second embodiment, the composition according to the invention may be ingested in the form of a liquid and notably in the form of a viscous liquid or a gel and notably a syrup.

The invention also relates to a capsule with a core/shell structure comprising at least one core consisting of a composition according to the invention and at least one coating layer completely or partly covering the surface of the core.

According to a first embodiment, the capsule core is in the form of a powder.

According to a second embodiment, the capsule core is in the form of a viscous liquid or a gel.

The invention also relates to a dietary kit comprising, preferably in two separate parts of one and the same packaging:

a composition according to the invention, and a portion of food.

The formulation of a composition according to the invention in the form of a kit is advantageous in that it makes it possible to supply the patients with pre-dosed, ready-to-use products corresponding to their needs for a meal.

In particular, the kit according to the invention may comprise a portion of food suitable for the patient's diet as well as a suitable dose of a composition according to the invention in an amount that gives the patient a sensation of satiety at the end of the meal.

The formulation in the form of a kit is also suitable for a snack to satisfy hunger between meals. In this precise case, the kit comprises a low-calorie portion of food and an additional dose of a composition according to the invention in an amount that gives the patient a sensation of satiety.

The invention also relates to a device for oral administration, such as for example a gavage syringe comprising a composition according to the invention.

This type of device is particularly suitable for administering a composition according to the invention to animals and notably to mammals.

The invention also relates to a food product for animals, and notably for mammals, said food product comprising a composition according to the invention.

The food product for animals may assume all the forms known by a person skilled in the art.

In particular, the food product for animals may be in the form of a pellet, a snack, a sweet or a biscuit.

Preferably, the food product for animals is in the form of a pellet.

The food product for animals is preferably soft.

The soft texture of a food product is advantageous in that it may have a more effective "appetite suppressing" effect by promoting chewing and therefore increasing the time for eating a meal.

A soft texture may be obtained in the absence of aqueous binders such as glycerol, which is generally used as a preservative.

Preferably, the food product for animals according to the invention comprises a core and a coating layer.

According to a first embodiment, the core is of a portion of food and the coating layer is of a composition according to the invention.

According to a second embodiment, the core is of a composition according to the invention and the coating layer is a portion of food.

Preferably, the core is of a portion of food and the coating layer is a composition according to the invention.

A portion of food suitable for an animal, for example a dog, comprises for example from 20 to 30 wt % of crude protein and from 10 to 20 wt % of fats, the remainder being carbohydrates and notably dietary fiber and ash.

The other constituents of the portion of food are not essential. Standard products may be incorporated.

The ingredients constituting the portion of food suitable for an animal may be selected so as to supply the animal that ingests it with all the recommended vitamins and minerals corresponding to a complete, balanced meal.

The portion of food suitable for an animal may notably comprise meat or a material derived from animals for example such as beef, chicken, turkey, lamb, fish, blood plasma, bone marrow and mixtures thereof.

The portion of food suitable for an animal may also not comprise meat but comprise a meat substitute such as soybean, maize gluten or a soy-based product as a source of proteins.

The portion of food suitable for an animal may also comprise other sources of proteins such as concentrates of soybean proteins, milk proteins, or gluten.

The portion of food suitable for an animal may also comprise a source of starch in the form of cereals notably selected from wheat, maize, rice, oat, barley and mixtures thereof.

Preferably, the portion of food suitable for an animal comprises at least one source of fiber.

Advantageously, the portion of food suitable for an animal comprises from 1 to 6 vol % of a composition according to the invention, the percentages being expressed in total volume of the food product.

Treatment

The invention also relates to a method for treating a human or animal patient to allow weight loss, said method comprising:

(1) supplying a suitable dose of a composition according to the invention,
(2) oral ingestion of the composition.

Oral ingestion of the composition allows the composition to reach the level of the patient's stomach.

Bringing the composition into contact with the gastric environment leads to swelling of the composition in contact with the gastric juice. The empty gastric volume is thus reduced and the patient experiences a sensation of satiety.

The method of treatment according to the invention is applied advantageously before the patient eats a meal.

Preferably, the meal is eaten by the patient directly after oral ingestion of the dose of composition according to the invention.

The dose of composition according to the invention to be ingested by the patient is determined by a medical practitioner, and notably by a dietician depending on the patient and his or her specific needs.

In particular, the dose of composition to be ingested by the patient is calculated as a function of his nutritional requirements but also as a function of the volume of his stomach in order to give him a sensation of satiety at the end of the meal.

According to a first embodiment, the patient has a volume of composition according to the invention and takes the appropriate dose by means of a suitable dosing device.

In particular, the dosing device is for example a graduated container, a syringe, a dosing spoon or a balance.

According to a second embodiment, the patient has the composition according to the invention in the form of a pre-dosed composition corresponding exactly to his needs.

FIGURES

FIG. 1a: graphical representation of the change in the degree of swelling of different compositions (ordinate) as a function of time in minutes (abscissa).

Curve 1 shows the variation of the degree of swelling of a composition according to the invention in which the foam stabilizer is Tween 80® (composition 1).

Curve 2 shows the variation of the degree of swelling of a composition according to the invention in which the foam stabilizer is gelatin (composition 2).

Curve 3 shows the variation of the degree of swelling of a composition free from foam stabilizer (composition 3).

Curves 4 and 5 are merged and show the variation of the degree of swelling of two compositions free from foaming agent (compositions 4 and 5 respectively).

Curve 6 shows the variation of the degree of swelling of a hydrogel composition as described in the prior art (composition 8).

Figure 1B:
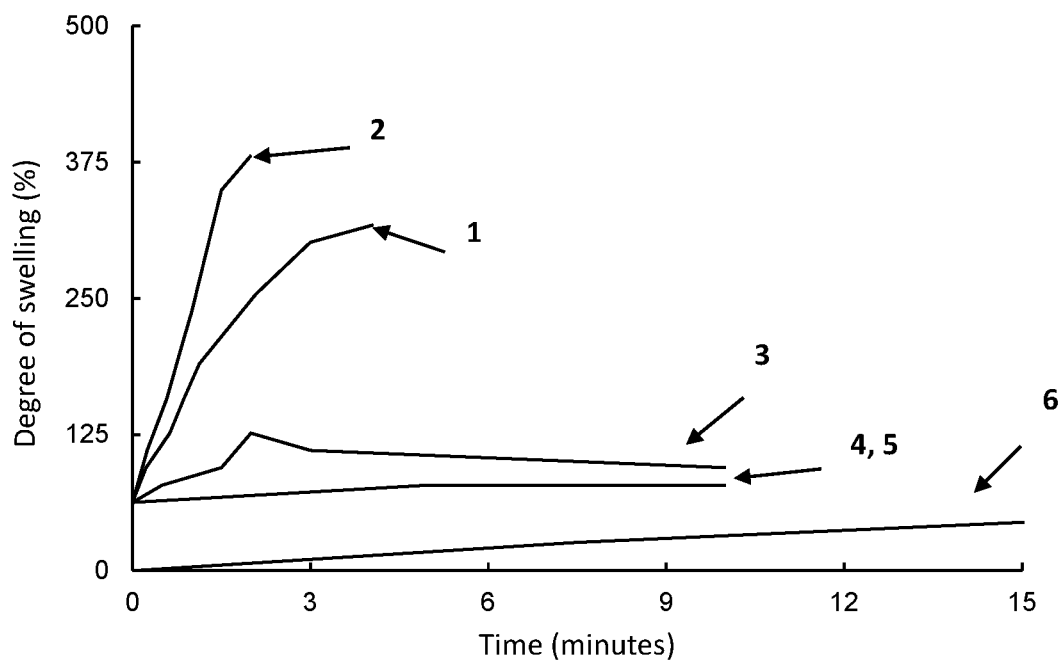

FIG. 1b: FIG. 1b is an enlarged detail of FIG. 1a corresponding to the time interval [0, 15 minutes].

Figure 2:
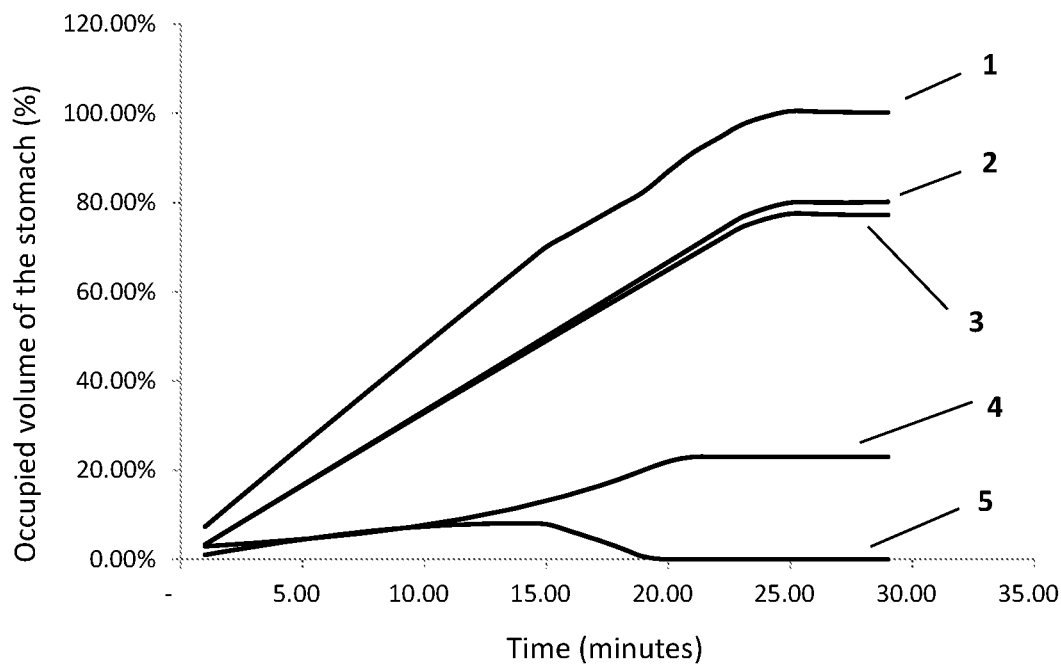

FIG. 2: graphical representation of the variation over time (abscissa) of the occupied volume of the stomach (ordinate) while eating a meal after ingesting a hydrogel composition of the prior art at t=0, the occupied volume of the stomach being expressed as a percentage of the total volume of the stomach.

Curve 1 shows the total occupied volume of the stomach (foodstuffs and liquid), the patient experiencing a sensation of satiety when this curve reaches 100%.

Curve 2 shows the volume of foodstuffs ingested by the patient.

Curve 3 shows the volume of foodstuffs present in the stomach.

Curve 4 shows the volume occupied by the ingested hydrogel.

Curve 5 shows the volume of liquid present in the stomach.

Figure 3:
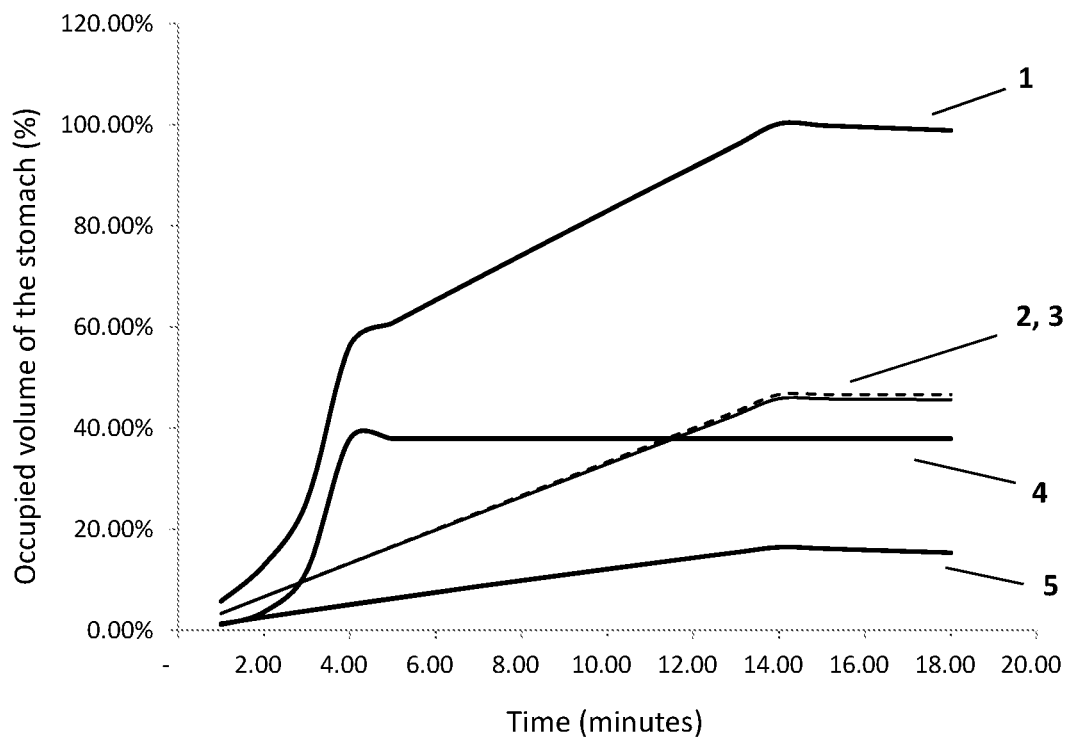

FIG. 3: graphical representation of the variation over time (abscissa) of the occupied volume of the stomach (ordinate) while eating a meal after ingesting a composition according to the invention at t=0, the occupied volume of the stomach being expressed as a percentage of the total volume of the stomach.

Curve 1 shows the total occupied volume of the stomach (foodstuffs and liquid), the patient experiencing a sensation of satiety when this curve reaches 100%.

Curve 2 (dashed line) shows the volume of foodstuffs ingested by the patient.

Curve 3 (solid line) shows the volume of foodstuffs present in the stomach.

Curve 4 shows the volume occupied by the ingested composition according to the invention.

Curve 5 shows the volume of liquid present in the stomach.

The invention is illustrated by the following nonlimiting examples.

EXPERIMENTAL SECTION

In these examples, the parts and percentages are expressed by weight unless stated otherwise.

Equipment and Reagents
Equipment:
- beaker,
- mechanical stirrer with anchor blade,
- heating plate,
- syringe and
- needle.

Reagents:
- water-soluble sodium alginate polymer (CAS: 9005-38-3), commercially available from Sigma Aldrich under reference A2033.
- calcium carbonate $CaCO_3$ (CAS: 471-34-1), commercially available from Sigma Aldrich under reference 398101.
- sodium bicarbonate $NaHCO_3$ (CAS: 144-55-8), commercially available from Sigma Aldrich under reference S5761.
- TWEEN 80® (CAS: 9005-65-6), commercially available from Sigma Aldrich under reference P1754.
- food gelatin derived from pigs in the form of plates commercially available from the company McCormick France SAS.
- citric acid (CAS: 77-92-9) in the form of an aqueous solution at 2.6%.

Protocol for Measuring the Variation of the Degree of Swelling of a Composition Over Time 2 mL of a composition according to the invention is put in a class A measuring cylinder graduated from 0 to 100 mL. 50 mL of an aqueous solution whose pH has been fixed at 2 by adding citric acid is then introduced carefully into the graduated measuring cylinder. It is important to introduce the aqueous solution into the graduated measuring cylinder carefully so as to be able to monitor the variation of the volume of the system.

The volume of the composition is recorded at regular intervals using a chronometer, between 10 s and 1 min depending on the measurement conditions.

The swelling of the composition is monitored until the volume stabilizes and reaches a plateau. The volume corresponding to this plateau is considered to be the volume corresponding to the maximum swelling of the composition in the conditions investigated. The degree of swelling of the composition is determined from the following equation:

$$G=(Vt-Vi)/Vi$$

with:
G: degree of swelling (without units)
Vt: volume determined at time t (in mL)
Vi: initial volume of the composition after drying (in mL)

The initial volume of the composition after drying Vi is determined as follows: 2 mL of the initial composition is poured into an aluminum dish with a diameter of 2 cm and put in an oven at 70° C. for 12 h. The dry product is then in the form of a disk with a diameter of 2 cm, the thickness of which is measured using a micrometer caliper gauge. The volume of this disk represents the initial volume of the composition after drying.

The measurements of swelling are repeated 3 times in order to determine an average degree of swelling.

Example 1: Preparation of the Compositions

Composition 1 (According to the Invention):

1 g of sodium alginate was dissolved in 46.9 mL of deionized water (concentration fixed at 20 g/L-2 wt % of alginate) with stirring with a motor and an anchor blade until a homogeneous solution was obtained (without aggregates of undissolved sodium alginate).

1 g of calcium carbonate $CaCO_3$ and 1 g of sodium bicarbonate $NaHCO_3$ were dispersed in the sodium alginate stock solution, stirring with an anchor blade until a homogeneous dispersion was obtained.

Finally, 100 mg of a mixture of surfactants (TWEEN 80®) was added to the dispersion.

Composition 2 (According to the Invention):

1 g of sodium alginate was dissolved in 46.9 mL of deionized water (concentration fixed at 20 g/L-2 wt % of alginate) with stirring with a motor and an anchor blade until a homogeneous solution was obtained (without aggregates of undissolved sodium alginate).

1 g of calcium carbonate $CaCO_3$ and 1 g of sodium bicarbonate $NaHCO_3$ were dispersed in the sodium alginate stock solution, stirring with an anchor blade until a homogeneous dispersion was obtained.

Finally, 100 mg of a structure-forming agent (gelatin) was added to the dispersion.

Composition 3 (Comparative, without Foam Stabilizer):

1 g of sodium alginate was dissolved in 47 mL of deionized water (concentration fixed at 20 g/L-2 wt % of alginate) with stirring with a motor and an anchor blade until a homogeneous solution was obtained (without aggregates of undissolved sodium alginate).

1 g of calcium carbonate $CaCO_3$ and 1 g of sodium bicarbonate $NaHCO_3$ were dispersed in the sodium alginate stock solution, stirring with an anchor blade until a homogeneous dispersion was obtained.

Composition 4 (Comparative, without Foaming Agent):

1 g of sodium alginate was dissolved in 47.9 mL of deionized water (concentration fixed at 20 g/L-2 wt % of alginate) with stirring with a motor and an anchor blade until a homogeneous solution was obtained (without aggregates of undissolved sodium alginate).

1 g of calcium carbonate $CaCO_3$ was dispersed in the sodium alginate stock solution, stirring with an anchor blade until a homogeneous dispersion was obtained.

Finally, 100 mg of a mixture of surfactants (TWEEN 80®) was added to the dispersion.

Composition 5 (Comparative, without Foaming Agent):

1 g of sodium alginate was dissolved in 47.9 mL of deionized water (concentration fixed at 20 g/L-2 wt % of alginate) with stirring with a motor and an anchor blade until a homogeneous solution was obtained (without aggregates of undissolved sodium alginate).

1 g of calcium carbonate $CaCO_3$ was dispersed in the sodium alginate stock solution, stirring with an anchor blade until a homogeneous dispersion was obtained.

Finally, 100 mg of a structure-forming agent (gelatin) was added to the dispersion.

Composition 6 (Comparative, without Compound Capable of Crosslinking the Hydrophilic Polymer by Forming Ionic Bonds):

1 g of sodium alginate was dissolved in 47.9 mL of deionized water (concentration fixed at 20 g/L-2 wt % of alginate) with stirring with a motor and an anchor blade until a homogeneous solution was obtained (without aggregates of undissolved sodium alginate).

1 g of sodium bicarbonate $NaHCO_3$ was dispersed in the sodium alginate stock solution, stirring with an anchor blade until a homogeneous dispersion was obtained.

Finally, 100 mg of a mixture of surfactants (TWEEN 80®) was added to the dispersion.

Composition 7 (Comparative, without Compound Capable of Crosslinking the Hydrophilic Polymer by Forming Ionic Bonds):

1 g of sodium alginate was dissolved in 47.9 mL of deionized water (concentration fixed at 20 g/L-2 wt % of alginate) with stirring with a motor and an anchor blade until a homogeneous solution was obtained (without aggregates of undissolved sodium alginate).

1 g of sodium bicarbonate $NaHCO_3$ was dispersed in the sodium alginate stock solution, stirring with an anchor blade until a homogeneous dispersion was obtained.

Finally, 100 mg of a structure-forming agent (gelatin) was added to the dispersion.

Composition 8 (Comparative, According to the Prior Art):

Composition 8 corresponds to a composition of the hydrogel type obtained from polyacrylamide.

It corresponds to the composition studied in the scientific article T. BERTRAND et al., *Dynamics of Swelling and Drying in a Spherical Gel*, PHYS. REV. APPLIED, Vol. 6, 2016.

Example 2: Comparison of the Variation of the Degree of Swelling as a Function of Time of Compositions According to the Invention Relative to a Composition of the Prior Art The variation of the degree of swelling of the compositions according to the invention 1 and 2 was determined according to the measurement protocol described above.

The results obtained are shown in FIGS. 1a and 1b, where curves 1 and 2 correspond respectively to the results obtained for composition 1 and for composition 2, according to the invention.

The degree of swelling of composition 8 of the hydrogel type according to the prior art was evaluated from the experimental data presented in the article T. BERTRAND et al., *Dynamics of Swelling and Drying in a Spherical Gel*, PHYS. REV. APPLIED, Vol. 6, 2016.

The variation over time of the radius of beads of hydrogel corresponding to composition 8 is presented in FIG. 1a) of that article.

By regarding these beads of hydrogel as spheres, it is possible, starting from their radius r, to calculate their volume at each instant by applying the following formula (I):

$$V=4/3\pi r^3 \tag{1}$$

From the volume occupied at each instant, it is possible to deduce the degree of swelling of the hydrogel at each instant by subtracting from it the volume occupied initially by the composition and then dividing the result for the difference by the initial volume occupied by the composition.

The results obtained are shown in FIGS. 1a and 1b, curve 6.

Referring to FIGS. 1a and 1b, curve 1 shows the variation of the degree of swelling of composition 1 according to the invention, curve 2 shows the variation of the degree of swelling of composition 2 according to the invention, and curve 6 shows the variation of the degree of swelling of composition 8, according to the prior art.

The maximum swelling observed for composition 8, according to the prior art, is reached in 240 minutes and corresponds to a degree of swelling of 261.

The maximum degree of swelling observed for composition 1 according to the invention is reached in 4 minutes in contact with the acid medium and corresponds to a degree of swelling of 318.

The maximum swelling observed for composition 2 according to the invention is reached in 2 minutes in contact with the acid medium and corresponds to a degree of swelling of 381.

Thus, compositions 1 and 2, according to the invention, have a degree of swelling greater than that of composition 8, according to the prior art. Moreover, this greater swelling is reached in a much shorter time: between 2 and 4 minutes for a composition according to the invention and about 4 hours for a composition according to the prior art.

In conclusion, the kinetics of swelling of compositions 1 and 3, according to the invention, is much quicker than that of composition 8, according to the prior art. Compositions 1 and 2, according to the invention, are therefore able to give the patient a sensation of satiety much more quickly than the hydrogel composition of the prior art.

Example 3: Simulation of the Volume Distribution of the Stomach Contents when Eating a Meal after Ingesting a Composition According to the Invention or a Composition According to the Prior Art The results obtained in example 2 were used for simulating the volume distribution of the stomach contents when eating a meal and after ingestion firstly of a composition of the hydrogel type according to the prior art (composition 8), and secondly of a composition according to the invention (composition 1). The results obtained are presented in FIGS. 2 and 3.

The time for eating a meal is on average 30 minutes. The model proposed is based on ingestion of hydrogel at the start of a meal, and then ingestion of foodstuffs until satiety is attained, evaluation taking place over a time of 30 minutes.

Composition 8:

Referring to FIG. 2:

Curve 1 shows the total occupied volume of the stomach.

Curve 2 shows the volume of foodstuffs ingested by the patient.

Curve 3 shows the volume of foodstuffs present in the stomach.

Curve 4 shows the volume of the stomach occupied by the hydrogel, according to the prior art.

Curve 5 shows the volume of liquid present in the stomach.

The patient experiences a sensation of satiety when the whole volume of the stomach is occupied, or when curve 1 reaches 100%.

A patient who has ingested a hydrogel according to the prior art therefore experiences a sensation of satiety 25 minutes after starting the meal.

At this precise moment, the volume distribution of the stomach is as follows:
- 23% of the total volume of the stomach is occupied by the hydrogel (curve 4), and
- 77% of the total volume of the stomach is occupied by the foodstuffs ingested by the patient while eating the meal (curve 3).

Since part of the food ingested has already passed into the intestine, the patient has in point of fact ingested a volume of foodstuffs equivalent to 80% of the total volume of the stomach (curve 2).

It is also observed that the volume of liquid present in the stomach (curve 5) decreases starting from 15 minutes after taking the hydrogel and becomes almost zero starting from 20 minutes after ingestion of the hydrogel.

This variation of the volume of liquid present in the stomach is evidence of the mechanism of swelling of the hydrogel according to the prior art: by absorption of water.

Composition 1:
Referring to FIG. 3:
Curve 1 shows the total occupied volume of the stomach.
Curve 2 (dashed line) shows the volume of foodstuffs ingested by the patient.
Curve 3 (solid line) shows the volume of foodstuffs present in the patient's stomach.
Curve 4 shows the volume occupied by the composition according to the invention.
Curve 5 shows the volume of liquid present in the stomach.

The patient experiences a sensation of satiety when the whole volume of the stomach is occupied, or when curve 1 reaches 100%.

A patient who has ingested a hydrogel according to the prior art therefore experiences a sensation of satiety 14 minutes after starting the meal.

At this precise moment, the volume distribution of the stomach is as follows:
38% of the total volume of the stomach is occupied by the composition according to the invention, and
46% of the total volume of the stomach is occupied by the foodstuffs ingested by the patient while eating the meal.
Satiety is reached more quickly in this second case.

As a result, the volume of food ingested by the patient and the volume of foodstuffs present in the stomach are almost equal: a very small amount of foodstuffs has had time to pass into the intestine.

The remaining volume of the stomach is occupied by liquids (curve 5).

It will also be noted that the volume of liquid present in the stomach does not decrease while eating the meal. Swelling of the composition according to the invention does not require absorption of liquid.

In both cases, the compositions according to the invention and according to the prior art make it possible to reduce the volume of foodstuffs ingested by a patient in order to experience a sensation of satiety.

Ingestion of a composition according to the invention gives a larger decrease of the volume of the foodstuffs ingested by the patient.

In fact the sensation of satiety is experienced by the patient who has ingested a composition according to the invention after 14 minutes. The volume of foodstuffs ingested by the patient represents at this precise moment 47% of the total volume of the stomach.

However, the sensation of satiety is experienced by the patient who has ingested a composition according to the prior art (composition 8) after 25 minutes. The volume of foodstuffs ingested by the patient represents at this precise moment 80% of the total volume of the stomach.

The composition according to the invention therefore allows a sensation of satiety to be attained more quickly.

Moreover, the composition according to the invention is a better "appetite suppressant", in that its ingestion at the start of a meal allows a greater decrease in the volume of foodstuffs to be ingested by a patient in order to experience a sensation of satiety.

Example 4: Influence of the Acidity of the Medium on the Degree of Swelling of the Composition The swelling properties of different compositions according to the invention were evaluated at neutral pH (compositions 1 and 2) and at pH equal to 4 (composition 2 only).

The protocol for measuring the degree of swelling of the compositions is similar to that described above, except that the aqueous composition is not at pH 2 but at pH 7 or 4.

The results are presented below.
Results:
Swelling at Neutral pH (pH=7)
In both cases, the compositions according to the invention (compositions 1 and 2) are simply diluted by the aqueous solution.

The phenomena of release of gases and crosslinking do not occur. An expanded foam of sodium alginate is not obtained.

Placed in a neutral medium, the composition according to the invention does not allow a hydrogel to be obtained in the form of an expanded foam.
Swelling at pH Equal to 4
No swelling is observed instantaneously after bringing composition 2 according to the invention into contact with the acid medium (pH=4).

After 1 minute in contact with the acid medium, the composition according to the invention begins to swell.

After 5 minutes, swelling of the composition has ended. The composition obtained has a low degree of swelling and the foam obtained is mechanically fragile.

Placed in an acid medium at pH equal to 4, the composition according to the invention allows a hydrogel foam to be obtained.

The degree of swelling of the composition is relatively low and the kinetics of swelling is slow.

Example 5: Influence of the Foam Stabilizer on the Degree of Swelling of the Composition The swelling properties of composition 3 (counter-example, free from foam stabilizer) were evaluated according to the protocol described above.

The results obtained are shown in FIGS. 1a and 1b, curve 3.

The maximum swelling observed for composition 3 is reached after 2 minutes in contact with the acid medium and corresponds to a degree of swelling of 126.

Thus, compositions 1 and 2 according to the invention have a degree of swelling from 2.5 to 3 times greater than that of composition 4 that is free from foam stabilizer.

The presence of a foam stabilizer in the compositions according to the invention therefore makes it possible to obtain a composition that is self-swelling in an acid medium and has a degree of swelling more than 2.5 times greater than that of a composition that is free from foam stabilizer.

Example 6: Influence of the Foaming Agent on the Degree of Swelling of the Composition The swelling properties of compositions 4 and 5 (counter-examples, free from foaming agent) were evaluated according to the protocol described above.

The results obtained are shown in FIGS. 1a and 1b, curves 4 and 5.

The results obtained for compositions 4 and 5 are very similar, curves 4 and 5 being merged.

The maximum swelling observed for compositions 4 and 5 is reached after 5 minutes in contact with the acid medium and corresponds to a degree of swelling of 79%.

Thus, compositions 1 and 2 according to the invention have a degree of swelling more than four times greater than that of compositions 4 and 5 free from foaming agent.

The presence of a foaming agent in the compositions according to the invention therefore makes it possible to obtain a composition that is self-swelling in an acid medium and has a high degree of swelling, notably more than 4 times greater than that of a composition free from foaming agent.

Example 7: Influence of the Agent Capable of Crosslinking the Polymer by Forming Ionic Bonds on the Degree of Swelling of the Composition The swelling properties of compositions 6 and 7 (counter-examples, free from compound capable of crosslinking the hydrophilic polymer by forming ionic bonds) were evaluated according to the protocol described above.

In both cases, the foaming agent is released by passage in an acid medium. We then observe formation of a foam that collapses quickly: the gas formed within the composition escapes from the hydrogel and does not allow a foam structure to be obtained.

Compositions 6 and 7 are simply diluted by the aqueous solution.

The presence of an agent capable of crosslinking the hydrophilic polymer by forming ionic bonds in the compositions allows a hydrogel to be obtained in the form of an expanded foam in an acid medium.

The invention claimed is:

1. A method for suppressing or reducing the appetite of a patient, the method comprising:
orally administering to the patient a composition capable of being transformed into a hydrogel foam after its introduction into the patient stomach,
wherein:
the hydrogel foam occupies at least 20% of the volume of the patient stomach,
the composition comprises:
a hydrophilic polymer selected from the group consisting of polysaccharides, polysaccharide derivatives, and mixtures thereof;
a compound (a) capable of crosslinking the hydrophilic polymer by forming ionic bonds, the compound (a) being selected from the group consisting of salts of divalent cations, salts of trivalent cations, and mixtures thereof;
a foaming agent (b) selected from the group consisting of salts capable of decomposing into gas and into monovalent cations; and
a foam stabilizer,
the compound (a) has a water solubility of less than or equal to 0.5 g/L at 20° C. and a pH of from 6.5 to 7.5, and has a pKa of less than or equal to 7.

2. The method as claimed in claim 1, wherein the hydrogel foam occupies at least 30% of the volume of the patient stomach.

3. The method as claimed in claim 1, wherein the composition is orally administered to the patient before the patient eats a meal.

4. The method as claimed in claim 1, wherein the oral administration of the composition provides the patient with a sensation of satiety that is reached more quickly than if the patient had not ingested the composition and/or reduces the volume of food ingested at each meal.

5. The method as claimed in claim 1, wherein the degree of swelling of the composition after its transformation into the hydrogel foam is greater than 300.

6. The method as claimed in claim 4, wherein the degree of swelling of the composition after its transformation into the hydrogel foam is greater than 500.

7. The method as claimed in claim 1, wherein the maximum swelling of the composition after its transformation into the hydrogel foam is reached in at most 10 minutes.

8. The method as claimed in claim 1, wherein the composition is a food supplement or a drug or a medical device.

9. The method as claimed in claim 1, wherein the patient is a human patient or an animal patient.

10. The method as claimed in claim 9, wherein the volume of the hydrogel foam after swelling in the human patient stomach is at least 200 ml.

11. The method as claimed in claim 10, wherein the volume of the hydrogel foam after swelling in the human patient stomach is at least 300 ml.

12. The method as claimed in claim 1, wherein the composition is administered in the form of a liquid or a gel or a solid.

13. The method as claimed in claim 1, wherein the ratio of the quantity of divalent and/or trivalent cations in the compound (a) to the quantity of monovalent cations in the compound (b) is greater than or equal to 0.05, the quantities of cations being expressed in moles.

14. The method as claimed in claim 1, wherein the content by weight of the hydrophilic polymer in the composition is from 10% to 99.5%, the content being expressed in weight of dry matter of the composition.

15. The method as claimed in claim 1, wherein the hydrophilic polymer is an alginate.

16. The method as claimed in claim 1, wherein the compound (a) is a carbonate of a divalent metal cation.

17. The method as claimed in claim 16, wherein the compound (a) is selected from the group consisting of calcium carbonate $CaCO_3$, manganese carbonate $MnCO_3$, silver carbonate $AgCO_3$, iron carbonate $FeCO_3$, copper carbonate $CuCO_3$, magnesium carbonate $MgCO_3$, and mixtures thereof.

18. The method as claimed in claim 1, wherein the foaming agent (b) is selected from the group consisting of sodium carbonate $Na_2CO_3$, sodium bicarbonate $NaHCO_3$, potassium bicarbonate $KHCO_3$, and mixtures thereof.

19. The method as claimed in claim 1, wherein the foam stabilizer is selected from the group consisting of structure-forming agents, surfactants, and mixtures thereof.

20. The method as claimed in claim 1, wherein:
the hydrophilic polymer is an alginate, and
the composition comprises:
from 0.01 to 50 wt % of at least one of the compound (a), each selected from the group consisting of carbonates of divalent metal cations, carbonates of trivalent metal cations, hydroxyapatite $Ca_{10}(PO_4)_6 OH_2$, and mixtures thereof; and
from 0.01 to 50 wt % of at least one of the compound (b), each selected from carbonates and bicarbonates of monovalent alkali metal cations.

21. The method as claimed in claim 1, wherein the composition is administered without prior or contemporaneous ingestion of water.

22. The method as claimed in claim 1, wherein the compound (a) has a water solubility of less than or equal to 0.1 g/L at 20° C. and a pH of from 6.5 to 7.5.

23. The method as claimed in claim 1, wherein the compound (a) has a pKa of less than or equal to 5.

* * * * *